(12) United States Patent
Perry

(10) Patent No.: US 9,113,894 B2
(45) Date of Patent: Aug. 25, 2015

(54) VEIN PRESENTATION ENHANCEMENT DEVICE

(76) Inventor: Robert J. Perry, Oklahoma City, OK (US)

( * ) Notice: Subject to any disclaimer, the term of this patent is extended or adjusted under 35 U.S.C. 154(b) by 489 days.

(21) Appl. No.: 13/478,945

(22) Filed: May 23, 2012

(65) Prior Publication Data

US 2013/0238013 A1 Sep. 12, 2013

Related U.S. Application Data

(63) Continuation-in-part of application No. 12/470,404, filed on May 21, 2009, now abandoned.

(60) Provisional application No. 61/054,961, filed on May 21, 2008.

(51) Int. Cl.
| | |
|---|---|
| *A61M 5/315* | (2006.01) |
| *A61B 17/135* | (2006.01) |
| *A61B 5/15* | (2006.01) |
| *A61M 5/42* | (2006.01) |
| *A61B 5/154* | (2006.01) |
| *A61M 25/06* | (2006.01) |

(52) U.S. Cl.
CPC ............. *A61B 17/135* (2013.01); *A61B 5/1438* (2013.01); *A61B 5/15003* (2013.01); *A61B 5/154* (2013.01); *A61B 5/150351* (2013.01); *A61B 5/150992* (2013.01); *A61M 5/31501* (2013.01); *A61M 5/31505* (2013.01); *A61M 5/31526* (2013.01); *A61M 5/42* (2013.01); *A61M 5/425* (2013.01); *A61M 5/427* (2013.01); *A61M 5/31511* (2013.01); *A61M 25/0631* (2013.01); *A61M 2005/31508* (2013.01)

(58) Field of Classification Search
CPC ... A61M 5/31526; A61M 5/42; A61M 5/425; A61M 5/427; A61B 5/154; A61B 17/135; A61B 5/15003; A61H 9/0078; A61H 9/0092
See application file for complete search history.

(56) References Cited

U.S. PATENT DOCUMENTS

| | | | |
|---|---|---|---|
| 4,664,651 A | 5/1987 | Weinshenker et al. | |
| 4,920,971 A * | 5/1990 | Blessinger | 600/492 |
| 4,941,458 A * | 7/1990 | Taheri | 601/152 |
| 5,109,832 A * | 5/1992 | Proctor et al. | 601/149 |
| 5,241,963 A * | 9/1993 | Shankar | 600/481 |

(Continued)

OTHER PUBLICATIONS

Non-final Office Action mailed Sep. 1, 2011 in U.S. Appl. No. 12/470,404.

(Continued)

*Primary Examiner* — Sean Dougherty
(74) *Attorney, Agent, or Firm* — San Diego IP Law Group LLP

(57) ABSTRACT

Preferably, an embodiment of a vein presentation enhancement device includes at least, an interior cover supporting a first fastening member, and an exterior cover communicating with the interior cover, wherein the exterior cover provides a first securement member that interacts with the first fastening member to secure the preferred device positioned about a limb of a subject. The preferred embodiment further includes a bladder formed between the interior and exterior covers, and an air transfer assembly connected to said bladder for transfer of air into and out of said bladder, wherein said interior and exterior covers collectively provide a plurality of projections defining a blood access window.

8 Claims, 28 Drawing Sheets

(56) References Cited

U.S. PATENT DOCUMENTS

| | | | | |
|---|---|---|---|---|
| 5,254,087 | A * | 10/1993 | McEwen | 604/66 |
| 5,380,295 | A | 1/1995 | Vacca | |
| 5,669,872 | A * | 9/1997 | Fox | 601/152 |
| 5,730,136 | A * | 3/1998 | Laufer et al. | 600/454 |
| 5,910,135 | A | 6/1999 | Hadzic et al. | |
| 6,010,470 | A * | 1/2000 | Albery et al. | 601/152 |
| 6,162,181 | A * | 12/2000 | Hynson et al. | 600/485 |
| 6,179,796 | B1 * | 1/2001 | Waldridge | 601/149 |
| 6,231,507 | B1 * | 5/2001 | Zikorus et al. | 600/437 |
| 6,364,843 | B1 | 4/2002 | Lightle | |
| 6,706,007 | B2 | 3/2004 | Gelfand et al. | |
| 7,175,809 | B2 | 2/2007 | Gelfand et al. | |
| 2003/0144691 | A1 * | 7/2003 | Lambroza | 606/202 |
| 2004/0097816 | A1 * | 5/2004 | Just et al. | 600/499 |
| 2004/0147956 | A1 * | 7/2004 | Hovanes et al. | 606/202 |
| 2005/0020977 | A1 * | 1/2005 | Eldridge et al. | 604/111 |
| 2005/0187500 | A1 * | 8/2005 | Perry et al. | 601/152 |
| 2007/0219580 | A1 | 9/2007 | McEwen et al. | |
| 2008/0245361 | A1 * | 10/2008 | Brown | 128/118.1 |
| 2008/0249440 | A1 * | 10/2008 | Avitable et al. | 601/151 |
| 2008/0249441 | A1 * | 10/2008 | Avitable et al. | 601/151 |
| 2008/0249442 | A1 * | 10/2008 | Brown et al. | 601/152 |
| 2008/0249443 | A1 * | 10/2008 | Avitable et al. | 601/152 |
| 2008/0249444 | A1 * | 10/2008 | Avitable et al. | 601/152 |
| 2008/0249447 | A1 * | 10/2008 | Brown et al. | 602/13 |
| 2008/0249449 | A1 * | 10/2008 | Brown et al. | 602/20 |
| 2008/0249559 | A1 * | 10/2008 | Brown et al. | 606/202 |
| 2008/0255485 | A1 * | 10/2008 | Johnson et al. | 601/149 |
| 2009/0240191 | A1 * | 9/2009 | Loori et al. | 604/23 |
| 2010/0210983 | A1 * | 8/2010 | Baker et al. | 601/152 |
| 2013/0245672 | A1 * | 9/2013 | Perry | 606/202 |

OTHER PUBLICATIONS

Response to Non-final Office Action filed Jan. 3, 2012 in U.S. Appl. No. 12/470,404.

Final Office Action mailed Feb. 9, 2012 in U.S. Appl. No. 12/470,404.

International Preliminary Report on Patentability and Written Opinion of the International Searching Authority for Int'l Application No. PCT/US2013/042317, mailed Nov. 25, 2014, 6 pages.

* cited by examiner

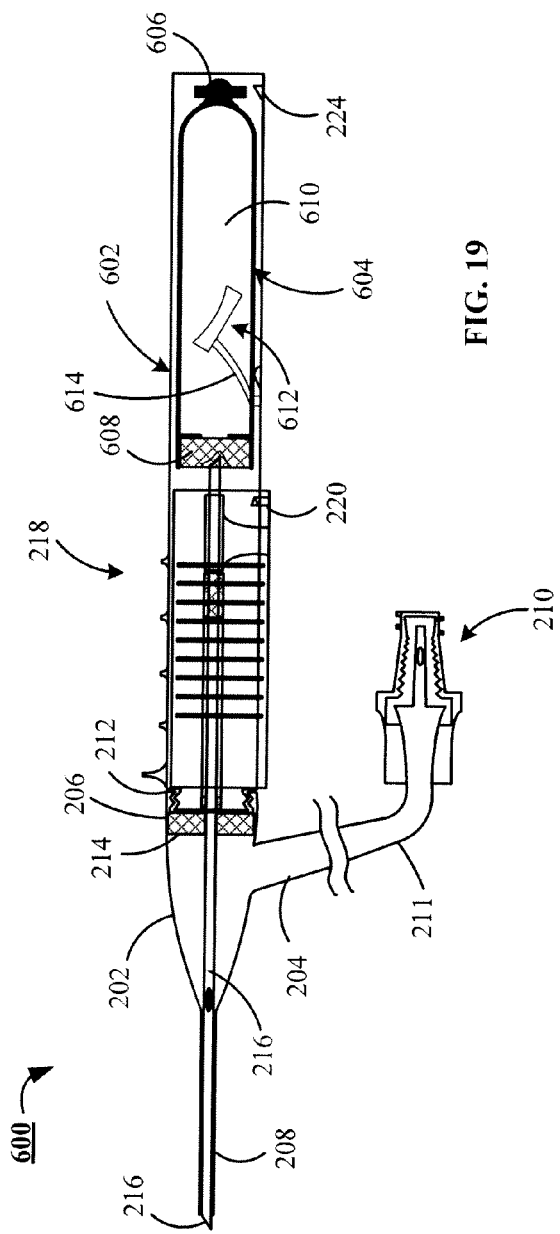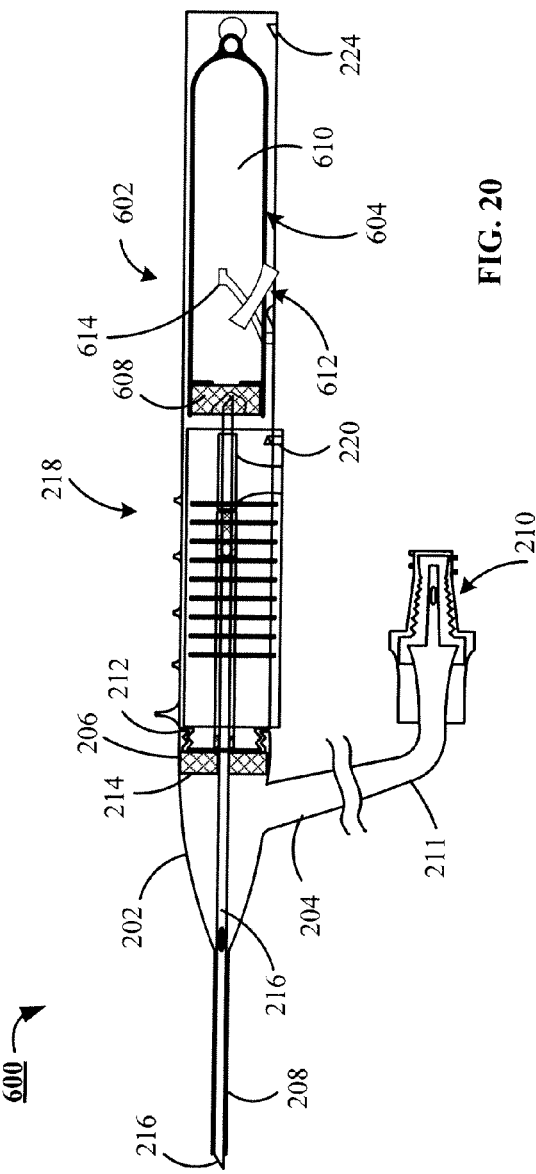

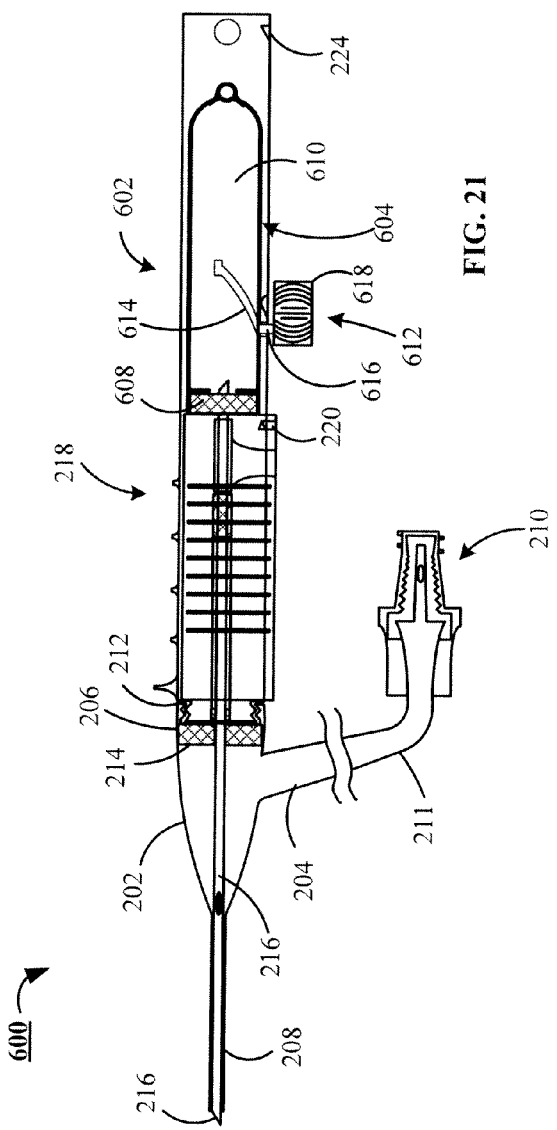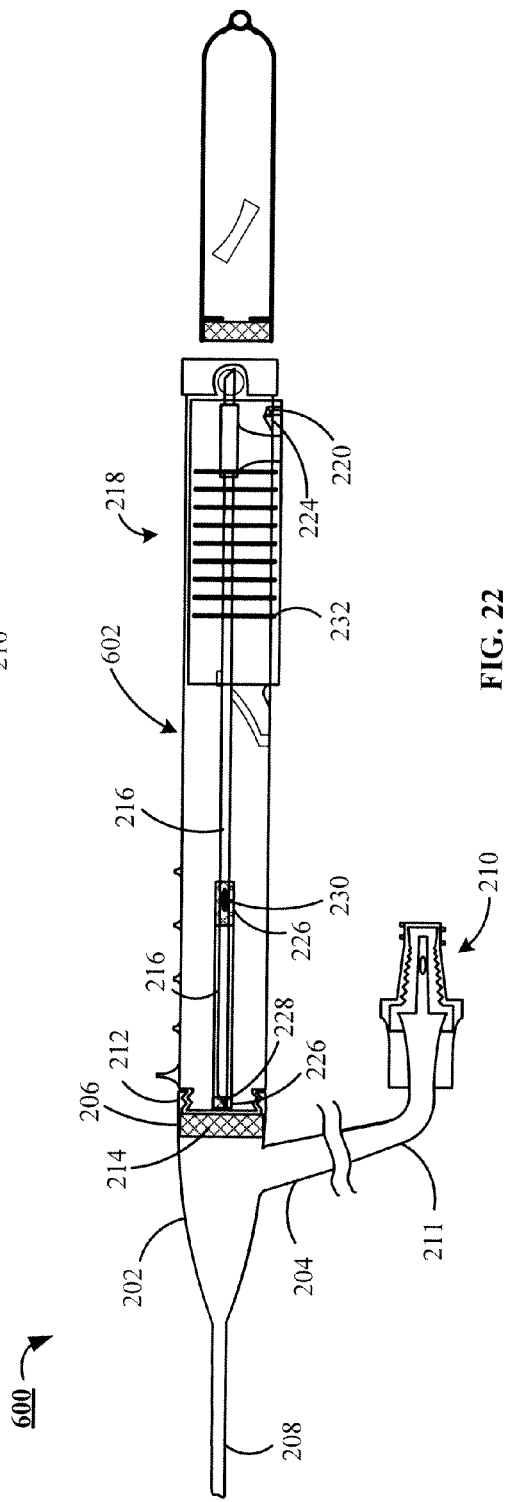
FIG. 21
FIG. 22

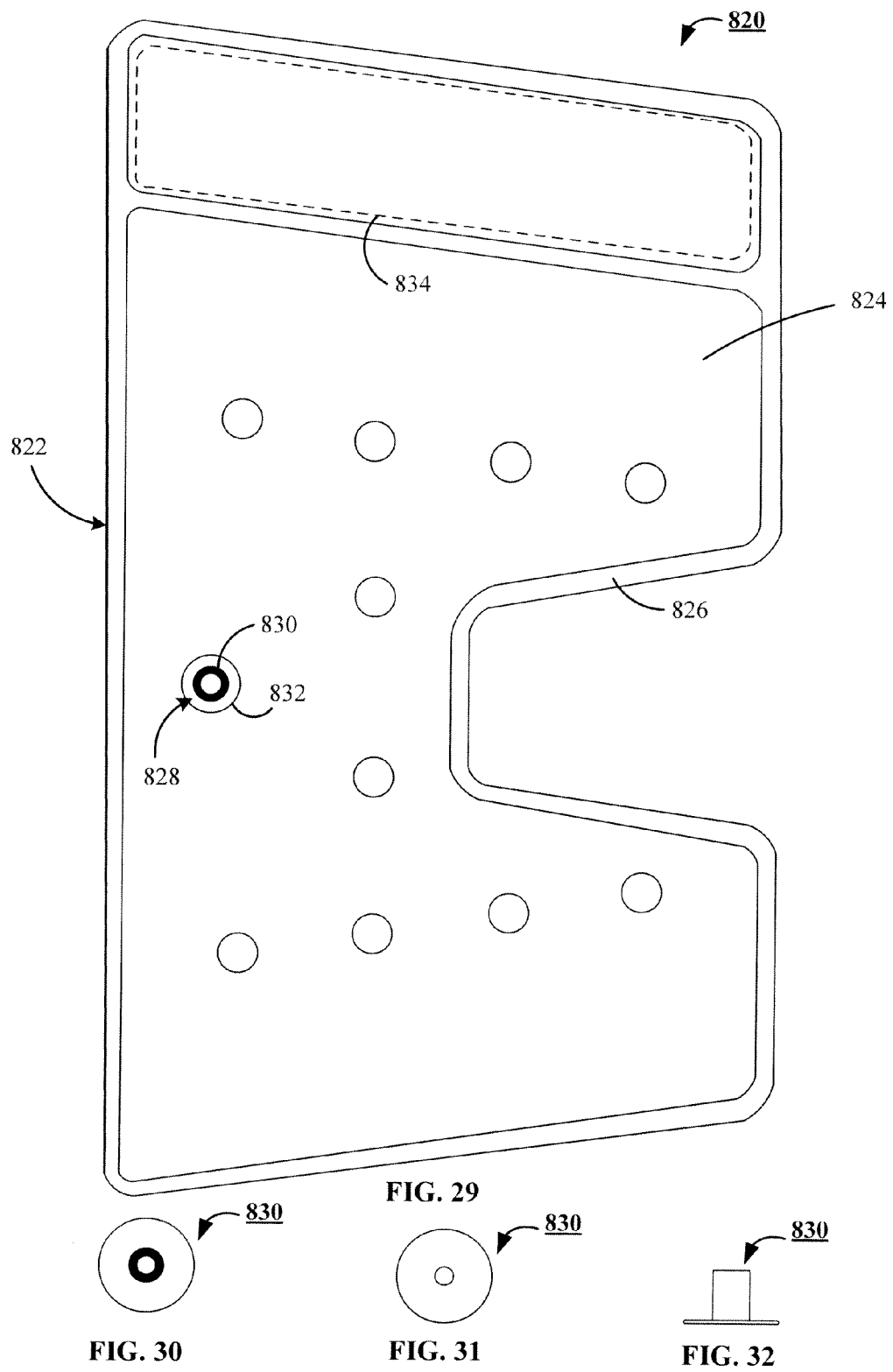

VEIN PRESENTATION ENHANCEMENT DEVICE

RELATED APPLICATIONS

This application is a continuation-in-part to U.S. patent application Ser. No. 12/470,404 filed May 21, 2009, which claims priority to Provisional Patent Application Ser. No. 61/054,961 filed May 21, 2008.

FIELD OF THE INVENTION

The present invention relates generally to the interaction of fluids with a blood vessel, but not by way of limitation, to the field of medical equipment.

BACKGROUND OF THE INVENTION

The ability to safely and efficiently interact fluids with blood vessels has been a continued need of the medical industry for generations.

Historically, the interaction of fluids with human blood vessels has been carried out through the conjunctive use of several fundamental medical instruments which are well known and in use by practitioners in the art. While these medical instruments reliably operate to interact with blood vessels, the safety and efficiency of using the instruments continues to pose a problem for the medical industry.

Accordingly, there is a continuing need for improved instruments and methods in the field of medical equipment.

SUMMARY OF THE INVENTION

In accordance with the exemplary embodiments, a preferred vein presentation enhancement device includes at least, an interior cover supporting a first fastening member, and an exterior cover communicating with the interior cover, wherein the exterior cover provides a first securement member that interacts with the first fastening member to secure the preferred device positioned about a limb of a subject. The preferred further includes a bladder formed between the interior and exterior covers, and an air transfer assembly connected to said bladder for transfer of air into and out of said bladder, wherein said interior and exterior covers collectively provide a plurality of projections defining a blood access window.

In an alternate preferred the vein presentation enhancement device is formed by steps that includes at least, providing an interior cover supporting a first fastening member, obtaining an exterior cover configured for communication with the interior cover, in which the exterior cover provides a first securement member, forming a bladder between said interior and exterior covers, and connecting an air transfer assembly to said bladder for transfer of air into and out of said bladder, wherein said interior and exterior covers collectively provide a plurality of projections defining a blood access window.

These and various other features and advantages which characterize the claimed invention will be apparent from reading the following detailed description and a review of the associated drawings.

BRIEF DESCRIPTION OF THE DRAWINGS

FIG. 19 is a partial cross-section elevation view of an alternate embodiment of the inventive exemplary embodiment of FIG. 5.

FIG. 20 is a partial cross-section elevation view of the alternate embodiment of FIG. 19 showing an advancement of a novel vacuum vile.

FIG. 21 is a partial cross-section elevation view of the alternate embodiment of FIG. 19 showing full advancement of the novel vacuum vile of FIG. 20.

FIG. 22 is a partial cross-section elevation view of the alternate embodiment of FIG. 19 showing a full retracted needle and separated novel vacuum vile of FIG. 21.

FIG. 29 is a top plan view of an alternative alternate exemplary embodiment of a novel blood channeling apparatus, also referred to as a vein presentation enhancement device.

FIG. 30 is a top plan view of a conduit interface member of the alternative alternate exemplary embodiment of the novel vein presentation enhancement device of FIG. 29.

FIG. 31 is a top plan view of a conduit interface member of the alternative alternate exemplary embodiment of the novel vein presentation enhancement device of FIG. 29.

FIG. 32 is a view in elevation of a conduit interface member of the alternative alternate exemplary embodiment of the novel vein presentation enhancement device of FIG. 29.

DETAILED DESCRIPTION OF THE INVENTION

Figure 1:
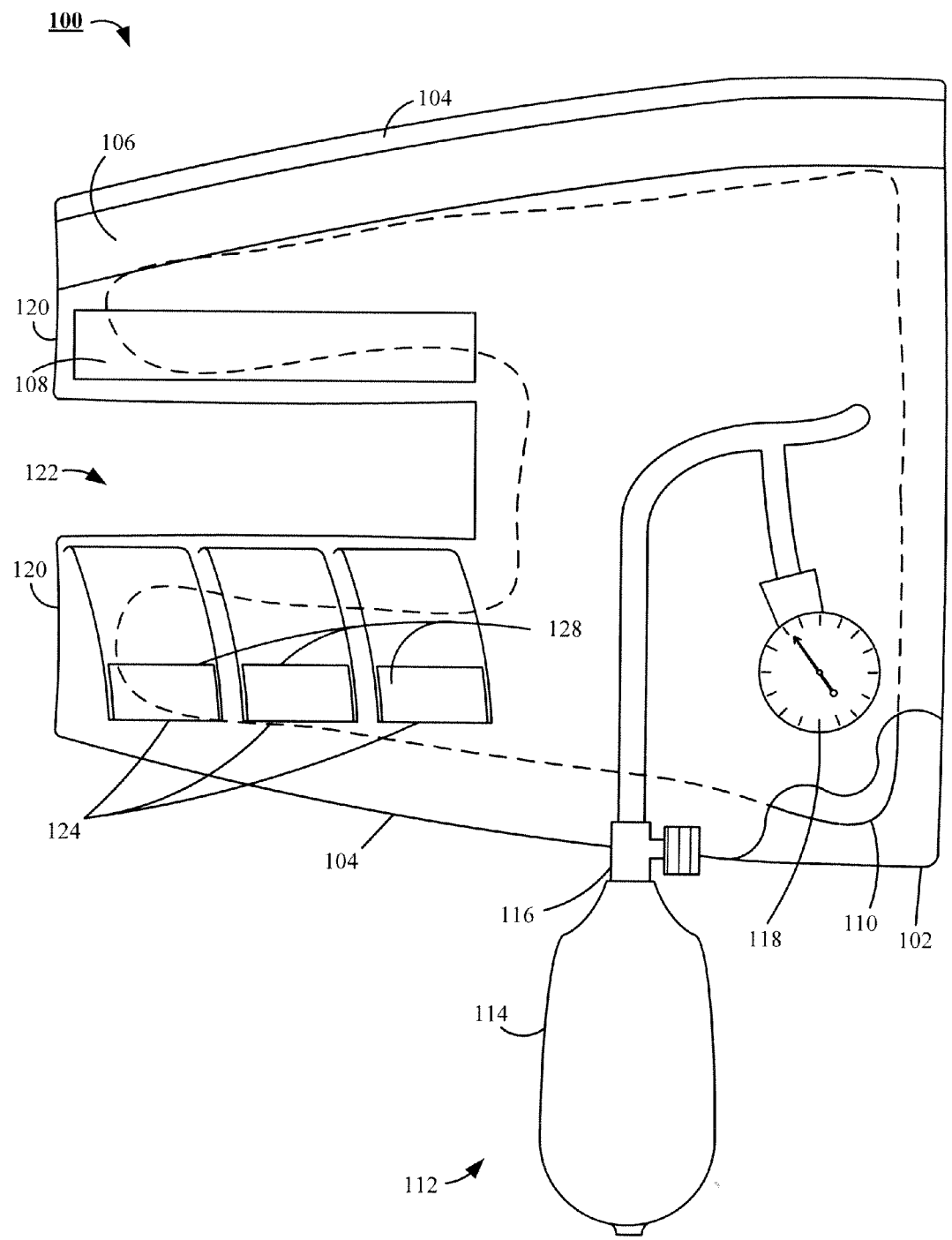
FIG. 1 is a partial cutaway top plan view of an exemplary embodiment of the novel blood channeling apparatus.

Exemplary embodiments of the present invention are generally directed to a blood vessel access kit configured to facilitate a transfer of fluids with a predetermined blood vessel. Reference will now be made in detail to the presently exemplary embodiments of the invention, one or more examples of which are illustrated in the accompanying drawings. Each example is provided by way of explanation of the invention, not limitation of the invention. In fact, it will be apparent to those skilled in the art that various modifications and variations can be made in the present invention without departing from the scope or spirit of the invention. For example, features illustrated or described as part of one embodiment, can be used on another embodiment to yield a still further embodiment. Thus, it is intended that the present invention cover such modifications and variations as come within the scope of the appended claims and their equivalents. Additionally, the numbering of components in the drawings is consistent throughout the application, with the same components having the same number in each of the drawings.

FIG. 1 shows an exemplary blood channeling apparatus 100 of an exemplary embodiment, also referred to herein as a vein presentation enhancement device 100. The exemplary blood channeling apparatus 100 includes an interior cover 102 secured to an exterior cover 104. The exterior cover 104 supports a first securement member 106 and a first fastening member 108. A bladder 110 is disposed between the interior cover 102 and the exterior cover 104. The bladder 110 serves to apply pressure to the extremity to encourage additional blood into a blood vessel of interest to accommodate the insertion of an intravenous ("IV") catheter into the blood vessel of interest.

To facilitate pressure build up and withdrawal, an air transfer assembly 112 communicates with the bladder 110. The air transfer assembly 112 includes at least an inflation mechanism 114, which may be of a manual or mechanical type; a valve 116, which selectively controls air flow into and out of the bladder 110; and a gauge 118, which may be of an analog or digital type and is provided to alert the practitioner to the amount of pressure present in the bladder 110.

In an exemplary embodiment, the interior cover 102 and exterior cover 104 join to form a plurality of projections 120 that define a window 122. In an exemplary embodiment, at least one attachment tab 124 is secured to one of the plurality of projections 120 and is configured for engagement with the first fastening member 108 secured to a corresponding projection 120, of the plurality of projections 120.

Figure 2:
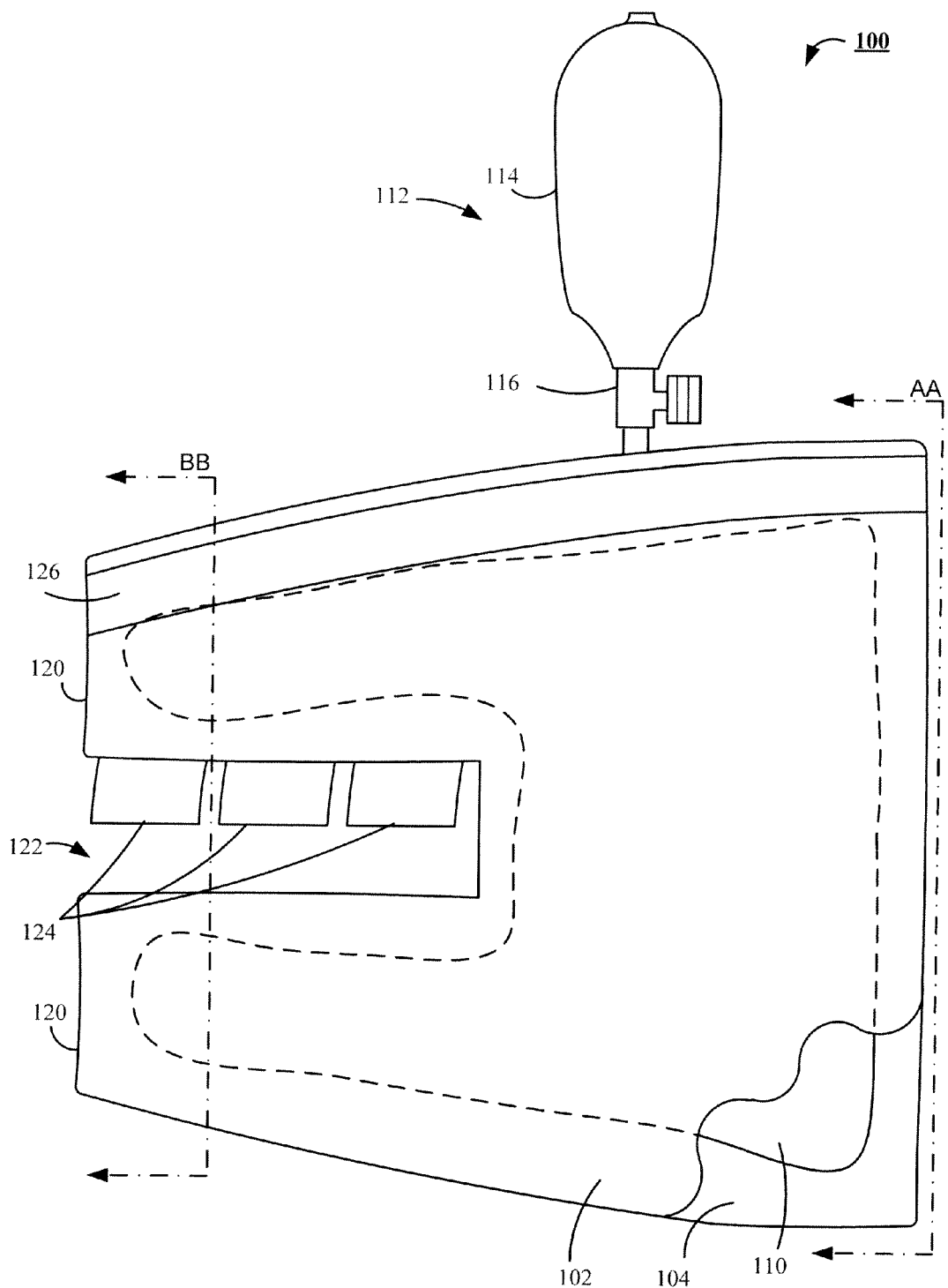
FIG. 2 is a partial cutaway bottom plan view of the exemplary embodiment of the novel blood channeling apparatus of FIG. 1.

FIG. 2 displays a bottom plan view of the exemplary blood channeling apparatus 100 of the exemplary embodiment. A second fastening member 126 is shown secured to the interior cover 102 of the exemplary blood channeling apparatus 100. The second fastening member 126 of the interior cover 102 is preferably configured to connect to the first securement member 106 of the exterior cover 104 to allow the exemplary blood channeling apparatus 100 to surround an extremity of a patient.

Figure 3:
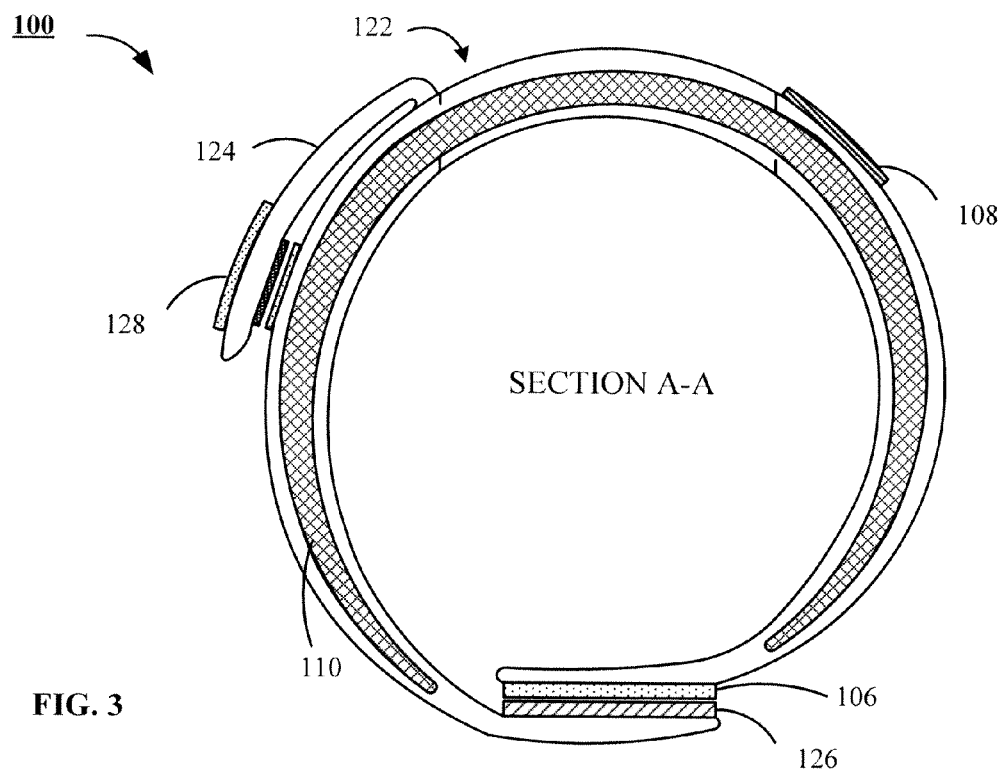
FIG. 3 is a cross-section side elevation view of the blood channeling apparatus at section line A-A of the exemplary embodiment, of FIG. 2.
Figure 4:
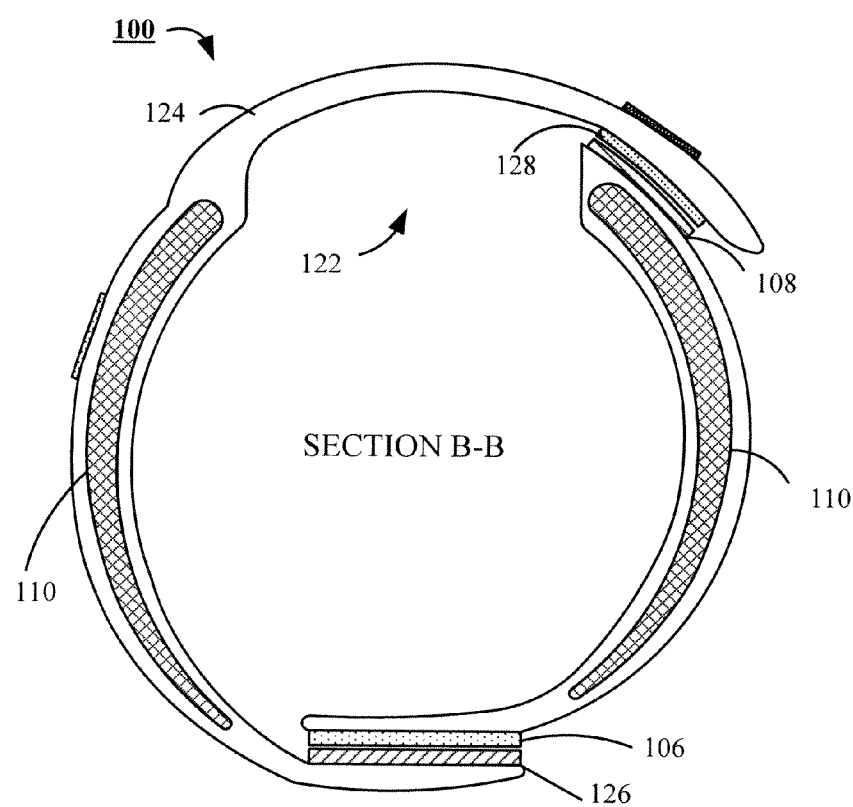
FIG. 4 is a cross-section side elevation view of the blood channeling apparatus at section line B-B of the exemplary embodiment, of FIG. 2.

FIG. 3 shows a view of section A-A of the exemplary blood channeling apparatus 100 in an exemplary embodiment of FIG. 2, indicative of a form consistent with the exemplary blood channeling apparatus 100 enclosing an appendage of a patient, at a distal end of a patient's appendage and adjacent an extremity of that appendage. Preferably, the window 122 of the exemplary blood channeling apparatus 100 can accommodate various dimensional sizes by varying an amount of overlap of a second securement member 128 (secured to the attachment tab 124), relative to the first fastening member 108 as seen by FIG. 4. Further in an exemplary embodiment, the first and second fastening members 108, 126 are loop portions of a hook and loop fastening system, while the first and second securement members 106, 128 are hook portions of a hook and loop fastening system. It is noted however that alternate fastening systems are contemplated, based on the specific use environment of the exemplary blood channeling apparatus 100. Preferably, the exemplary blood channeling apparatus 100 confines an extremity of a patient via the connection of the first securement member 106 and the second fastening member 126.

FIG. 4 shows a view of section B-B of the exemplary blood channeling apparatus 100 in an exemplary embodiment of FIG. 2, indicative of a form consistent with the exemplary blood channeling apparatus 100 enclosing an appendage of a patient, at a distal end of a patient's appendage and adjacent an extremity of that appendage. The attachment tab 124 of the exemplary blood channeling apparatus 100 is shown preferably configured to size the window 122. In an exemplary embodiment, a plurality of attachment tabs 124 can be connected to their corresponding first fastening member 108 of projection 120 of the interior and exterior covers 102 and 104, to provide several possible window sizes. Again, the size of the window 122 is determined by an amount of overlap of the second securement member 128 relative to the first fastening member 108.

Figure 5:
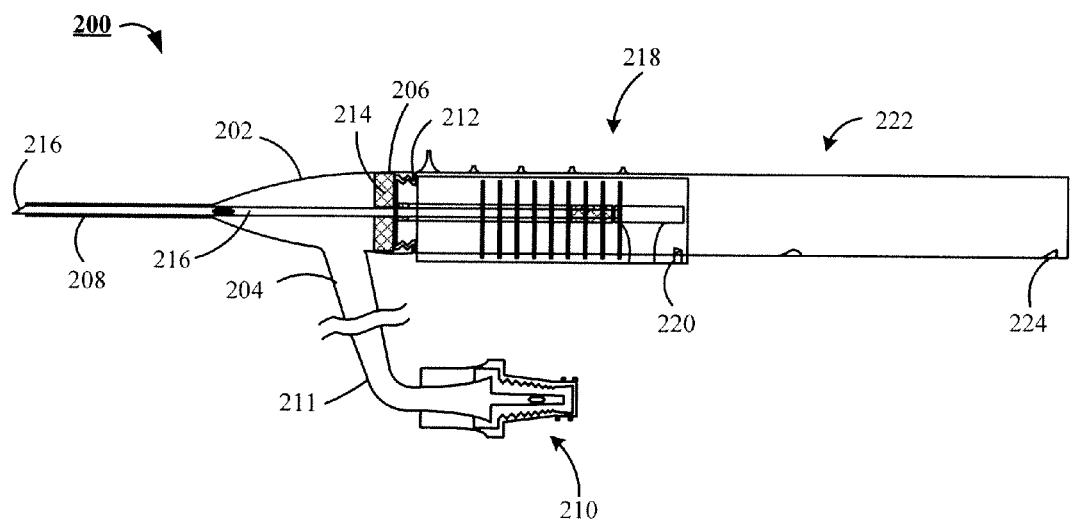
FIG. 5 is a side elevation view of an intravenous catheter in an exemplary embodiment.

FIG. 5 shows an exemplary intravenous catheter 200, which preferably includes at least a fluid chamber 202 that provides at least one conduit 204 and diaphragm housing 206. In an exemplary embodiment, the diaphragm housing 206 is located on the proximal end of the fluid chamber 202, and catheter 208 secured to the distal end of the fluid chamber 202. In a further exemplary embodiment, a needleless valve 210 communicates with the fluid chamber 202 via a fluid transfer tube 211 secured to and disposed between the conduit 204 and the needleless valve 210. The CLAVE® Connector with luer lock, such as those manufactured by ICU Medical Inc. of San Clemente Calif., has been found to be suitable as the needleless valve 210.

FIG. 5 further shows the fluid chamber 202 of the exemplary intravenous catheter 200 preferably has a securement member 212 adjacent the diaphragm housing 206. Preferably, a diaphragm 214 is confined in the diaphragm housing 206, and is configured to allow passage of a hypodermic needle 216, which extends from a needle transport 218 through the diaphragm 214, the fluid chamber 202, and the catheter 208 when the exemplary intravenous catheter 200 is configured for insertion into a predetermined blood vessel of a patient. The needle transport 218 includes a needle confinement feature 220, which interacts with a needle safety catch feature 224 to secure the hypodermic needle 216 within a needle confinement housing 222, once the hypodermic needle 216 has been extracted from the diaphragm 214.

Figure 6:
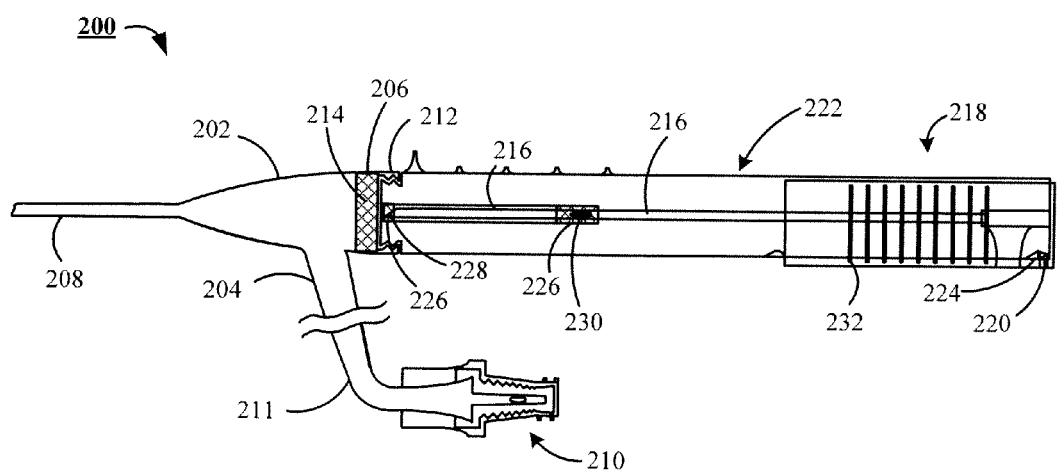
FIG. 6 is a side elevation view of the intravenous catheter of FIG. 5.

FIG. 6 shows the needle transport 218 of the exemplary intravenous catheter 200 preferably includes a plurality of isolation diaphragms 226 configured to enclose first and second fluid ports 228 and 230 of the hypodermic needle 216, when the needle confinement feature 220 is secured by the needle safety catch feature 224. Further in an exemplary embodiment, a grip portion 232 is provided by the needle transport 218 to facilitate sliding communication of the needle transport 218 with the needle confinement housing 222.

Figure 7:
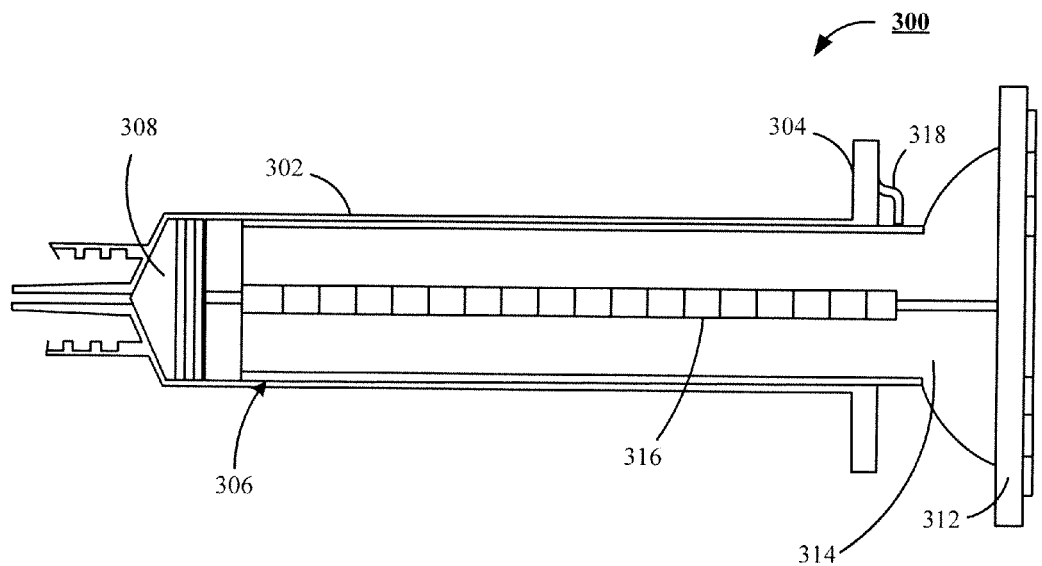
FIG. 7 is a partial cutaway elevation view of the syringe in an exemplary embodiment.

FIG. 7 shows an exemplary syringe 300 in an exemplary embodiment. The exemplary syringe 300 preferably comprises a hollow cylinder 302, shown in partial cut-away, which provides a support flange 304 on a proximal end of the hollow cylinder 302. In an exemplary embodiment, a piston 306 that includes at least a seal portion 308 positioned on a distal end and in sliding contact with an internal surface 310 (shown in FIG. 8) of the hollow cylinder 302, a piston activation member 312 on a proximal end, and a stem 314 disposed between the seal portion 308 and the piston activation member 312. The piston 306 selectively serves to draw fluids in and expel fluids from the hollow cylinder 302. In an exemplary embodiment, the stem provides a plurality of calibration notches 316, which when positioned into alignment with a stem control member 318, provided by the support flange 304, controls transfer of a precise volume of fluid drawn in or expelled from the hollow cylinder 302.

Figure 8:
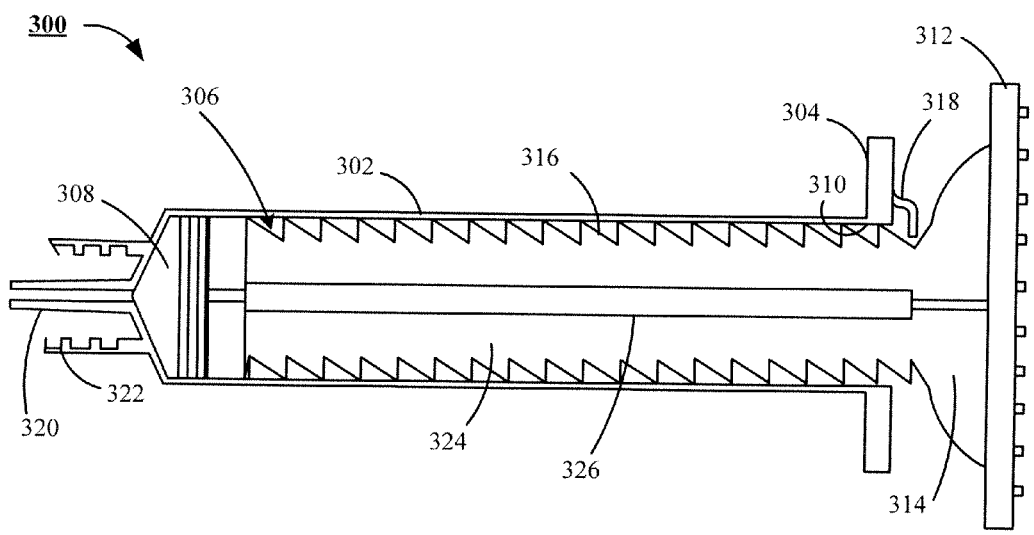
FIG. 8 is a partial cutaway elevation view of the syringe of FIG. 7.
Figure 9:
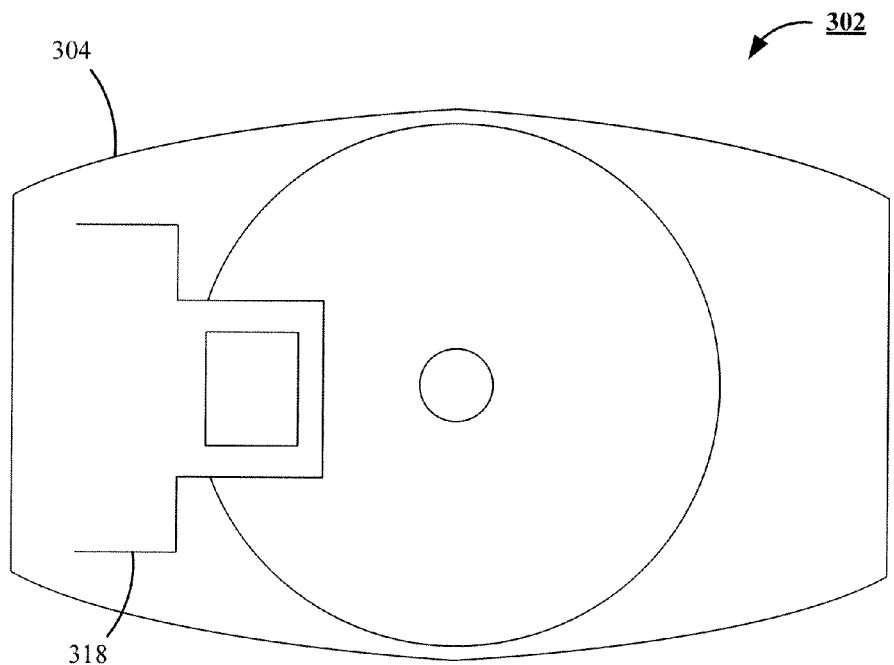
FIG. 9 is a top plan view of the hollow cylinder of the syringe of FIG. 7.

FIG. 8 further shows the exemplary syringe 300 of an exemplary embodiment includes a tapered portion (also referred to herein as a luer) 320 and a securement member 322 at the distal end of the hollow cylinder 302. The luer 320 and securement member 322 are at least configured to interact with a needleless valve 210 (of FIG. 5). FIG. 9 shows a top plan view of the hollow cylinder 302 of the exemplary syringe 300 in an exemplary embodiment. The stem control member 318 of the exemplary syringe 300 is preferably formed from a material, such as spring steel, but may be formed of any material that provides a spring like response, and is secured to, formed in or formed with the support flange 304 of the hollow cylinder 302. Preferably, the stem control member 318 interacts with the calibration notches 316 to control displacement of the piston 306 in the hollow cylinder 302.

Figure 10:
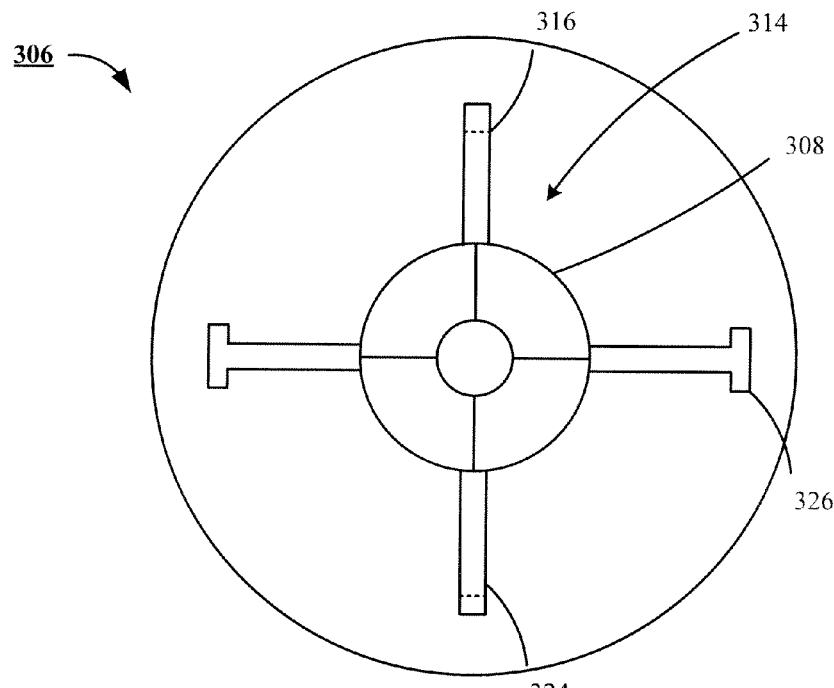
FIG. 10 is a bottom plan view of the stem of the syringe of FIG. 7.

FIG. 10 displays a bottom plan view of the piston 306 of the exemplary syringe 300 in an exemplary embodiment. The stem 314 of the exemplary syringe 300 preferably includes a plurality of fins 324 in which the calibration notches 316 are preferably located on at least two of the plurality of fins 324, while at least one alternate fin 324 of the plurality of fins 324 provide a land 326. In an exemplary embodiment, when the land 326 is aligned with the stem control member 318 (of FIG. 8), the piston 306 is free to move unencumbered within the hollow cylinder 302 (of FIG. 8), having only the sliding friction developed between the seal portion 308 and the internal surface 310 (shown in FIG. 8) of the hollow cylinder 302 to overcome.

Figure 11:
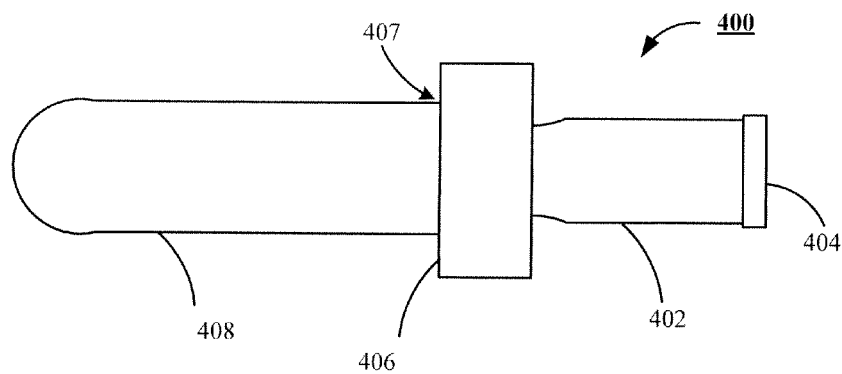
FIGS. 11 & 11A show an elevation view of a container in an exemplary embodiment.

FIG. 11 shows an exemplary container 400 of the exemplary embodiment that preferably includes at least a seal housing 402 supporting an access seal 404, which prevents inadvertent access to the interior of the seal housing 402. In an exemplary embodiment, the seal housing 402 is secured to a diaphragm 406 (also referred to herein as an inline coupling 406), which preferably surrounds a portion of a test tube 408 to form a vacuum seal 407 with the test tube 408 and present a vacuum charged blood collection tube.

Figure 11A:
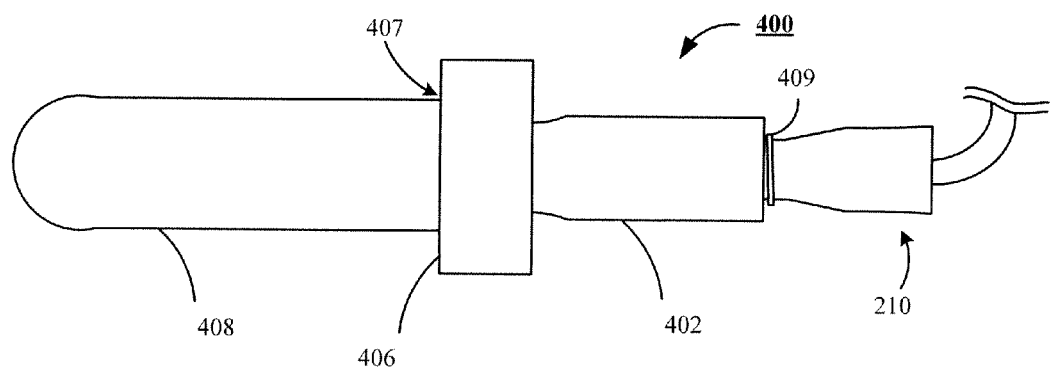

FIG. 11A shows the seal housing 402 of the exemplary container 400 is operatively connectable to at least the needleless valve 210 preferably via luer lock threads 409 provided by the needleless valve 210. In an exemplary embodiment, the seal housing 402 is secured to a diaphragm 406 (also referred to herein as an inline coupling 406), which preferably surrounds a portion of the test tube 408 to present a vacuum blood collection tube. Preferably, the inline coupling 406 of the exemplary container 400 forms a vacuum seal 407 with the test tube 408.

Figure 12:
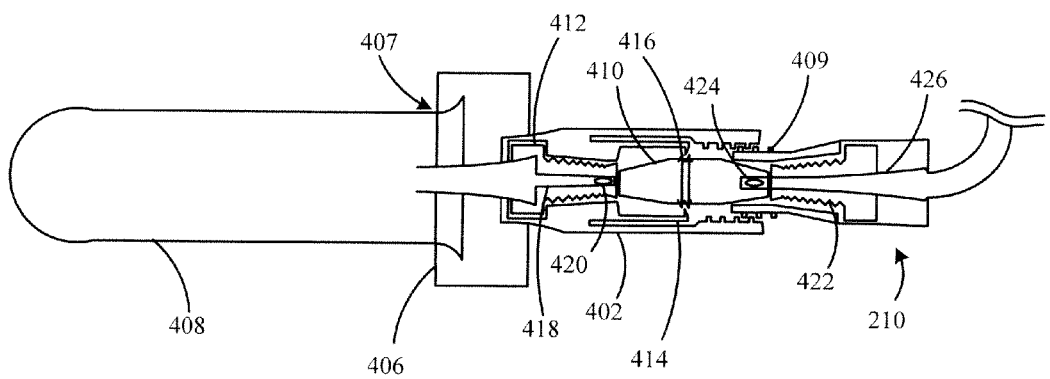
FIG. 12 is a cross-section elevation view of the container of FIG. 11.

FIG. 12 displays the exemplary container 400 in an exemplary embodiment that includes a bidirectional tapered luer 410 secured within the seal housing 402. The bidirectional tapered luer 410 is held in abutting adjacency against a resilient seal 412 by a plurality of retention fingers 414, provided by the seal housing 402, interacting with an annular retention collar 416 of the bidirectional tapered luer 410. In an exemplary embodiment, the seal housing 402 comprises a conduit 418 surrounded by the resilient seal 412. The conduit 418 of the exemplary container 400 further preferably comprises a fluid access port 420.

In an operative mode, upon an engagement of the needleless valve 210 by the exemplary container 400, the bidirectional tapered luer 410 interacts with a resilient seal 422 of the needleless valve 210 to expose a fluid port 424 of the needleless valve 210 in preparation for a transfer of fluid through a fluid tube 426 of the needleless valve 210. Upon further engagement of the exemplary container 400 with the needleless valve 210, the bidirectional tapered luer 410 interacts with the resilient seal 412 of the seal housing 402 to expose the fluid access port 420 of the conduit 418, which exposes the vacuum environment within the test tube 408 to pull fluid from the fluid tube 426 into the test tube 408. When pressure is equalized between the test tube 408 and the fluid tube 426, the exemplary container 400 is disengaged from the needleless valve 210 and the respective resilient seals 412 and 422 close off their respective fluid ports 420 and 424.

Figure 13:
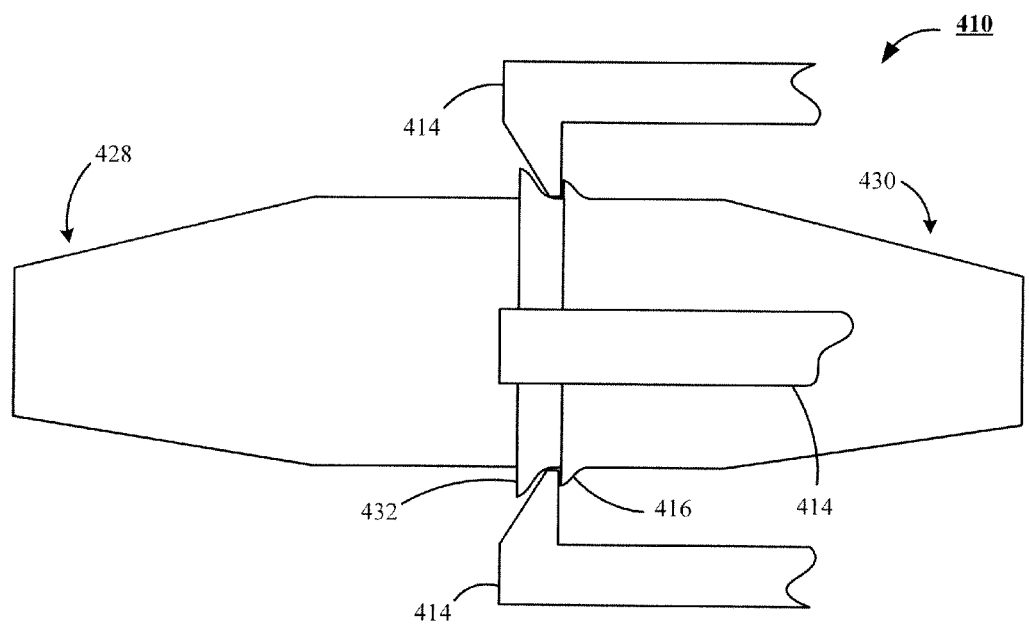
FIG. 13 is an elevation view of the bidirectional luer of the container of FIG. 12.

FIG. 13 shows the bidirectional tapered luer 410 of the exemplary container 400 (of FIG. 12) includes a first tapered end 428, a second tapered end 430, and a luer seating ridge 432. In an exemplary operating environment a vacuum is drawn on the test tube 408 (of FIG. 12) via the fluid port 420 (of FIG. 12), then the bidirectional tapered luer 410 is positioned within the seal housing 402 (of FIG. 12) such that the retention fingers 414 engage the retention collar 416, which positions the second tapered end 430 adjacent the resilient seal 412 (of FIG. 12) and confines the bidirectional tapered luer 410 within the seal housing 402.

Figure 14:
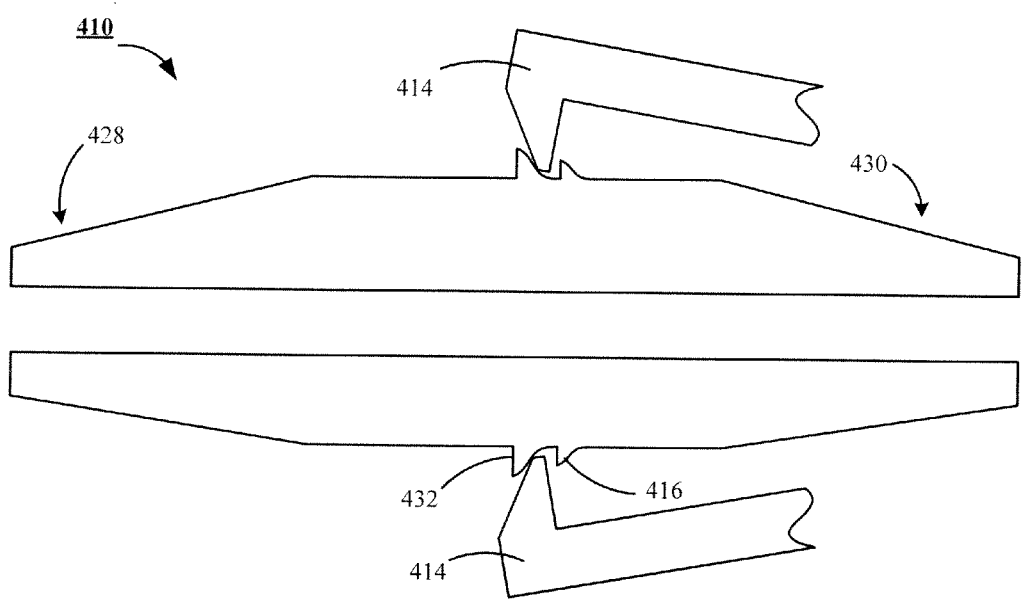
FIG. 14 is a cross-section elevation view of the bidirectional luer of the container of FIG. 12.

When the exemplary container 400 initially engages the needleless valve 210 (of FIG. 12), the first tapered end 428 of the bidirectional tapered luer 410 contacts the resilient seal 422 (of FIG. 12), and as the engagement of the exemplary container 400 with the needleless valve 210 progresses, the retention fingers 414 encounter the luer seating ridge 432 as shown by FIG. 14. For exemplary embodiment 400, preferably an amount of force required for the retention fingers 414 to pass by the luer seating ridge 432 is greater than the force needed to compress the resilient seal 422 of the needleless valve 210, and the resilient seal 422 compresses to open the fluid port 424 (of FIG. 12).

With continued advancement of the exemplary container 400 onto the needleless valve 210, the first tapered end 428 of the bidirectional tapered luer 410 bottoms out against the housing of the needleless valve 210; that is the housing encapsulating the resilient seal 422. With further advancement of the exemplary container 400 onto the needleless valve 210, the retention fingers 414 overcome the luer seating ridge 432, and second tapered end 430 compresses the resilient seal 412 of the housing 402, which opens the fluid port 420 of the housing 402 causing the vacuum within the test tube 408 to draw fluid from the fluid tube 426 into the test tube 408.

Figure 15:
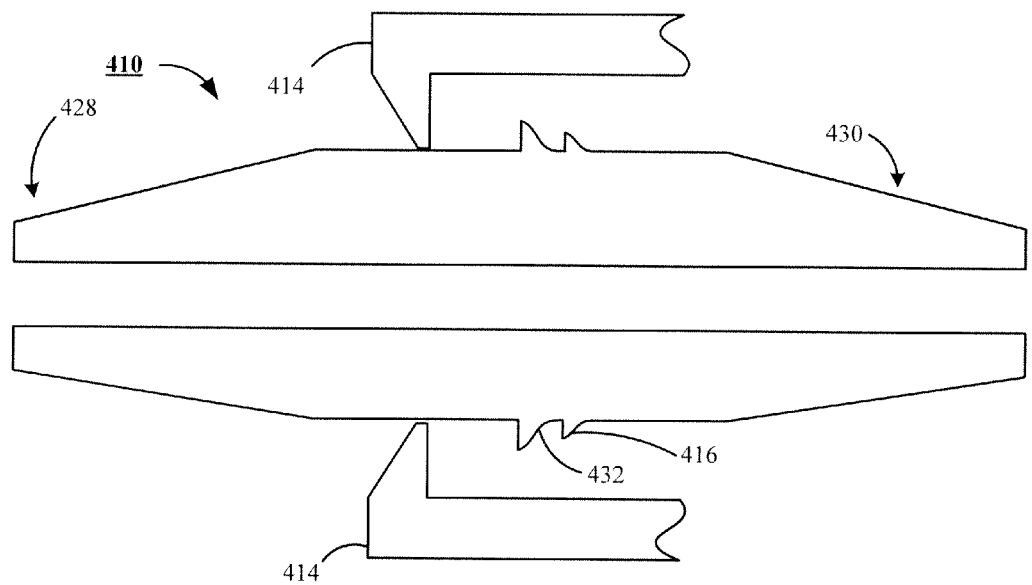
FIG. 15 is a cross-section elevation view of the bidirectional luer of the container of FIG. 12.
Figure 16:
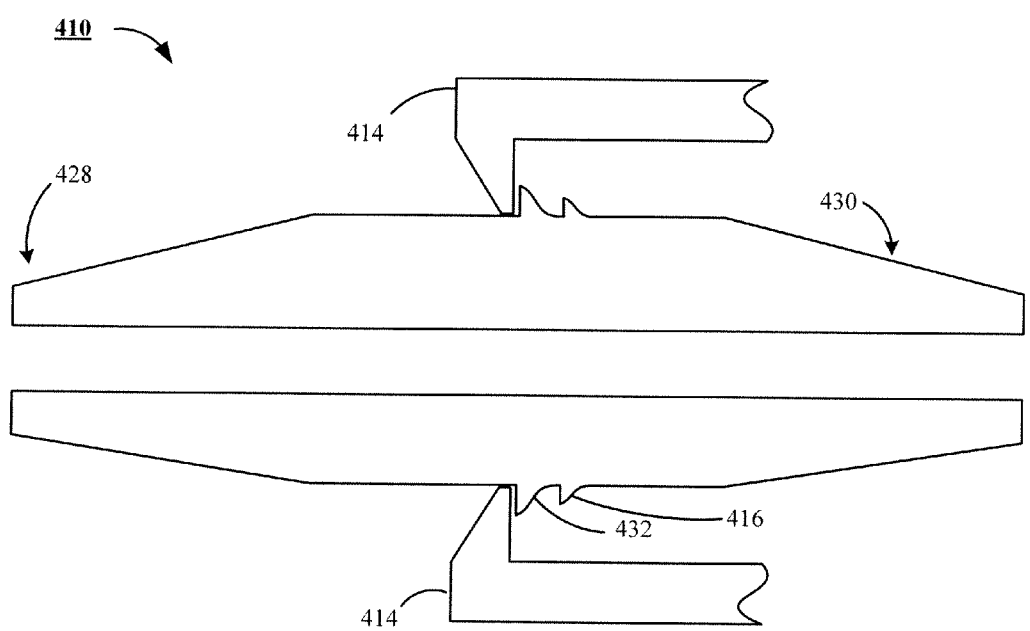
FIG. 16 is a cross-section elevation view of the bidirectional luer of the container of FIG. 12.

During fluid transfer, the retention fingers 414 are positioned, relative to the bidirectional tapered luer 410 as shown in FIG. 15, and upon disengagement of the exemplary container 400 from the needleless valve 210, the retention fingers 414 engage a top side of the luer seating ridge 432, as shown by FIG. 16. In an exemplary embodiment, both the luer seating ridge 432 and the retention collar 416 provide a contoured bottom surface and a flat top surface. The contoured bottom surface accommodates passage of the retention fingers 414 by the luer seating ridge 432 and the retention collar 416, while the flat top surfaces inhibit passage of the retention fingers 414 by the luer seating ridge 432 and the retention collar 416. Accordingly, when the retention fingers 414 are adjacent the flat surfaces, of either the luer seating ridge 432 or the retention collar 416, the bidirectional tapered luer 410 will remain confined within the housing 402. Removal of the bidirectional tapered luer 410 from the housing 402 is accomplished by encouraging the retention fingers 414 away from the luer seating ridge 432 or the retention collar 416 as the case may be.

Figure 17:
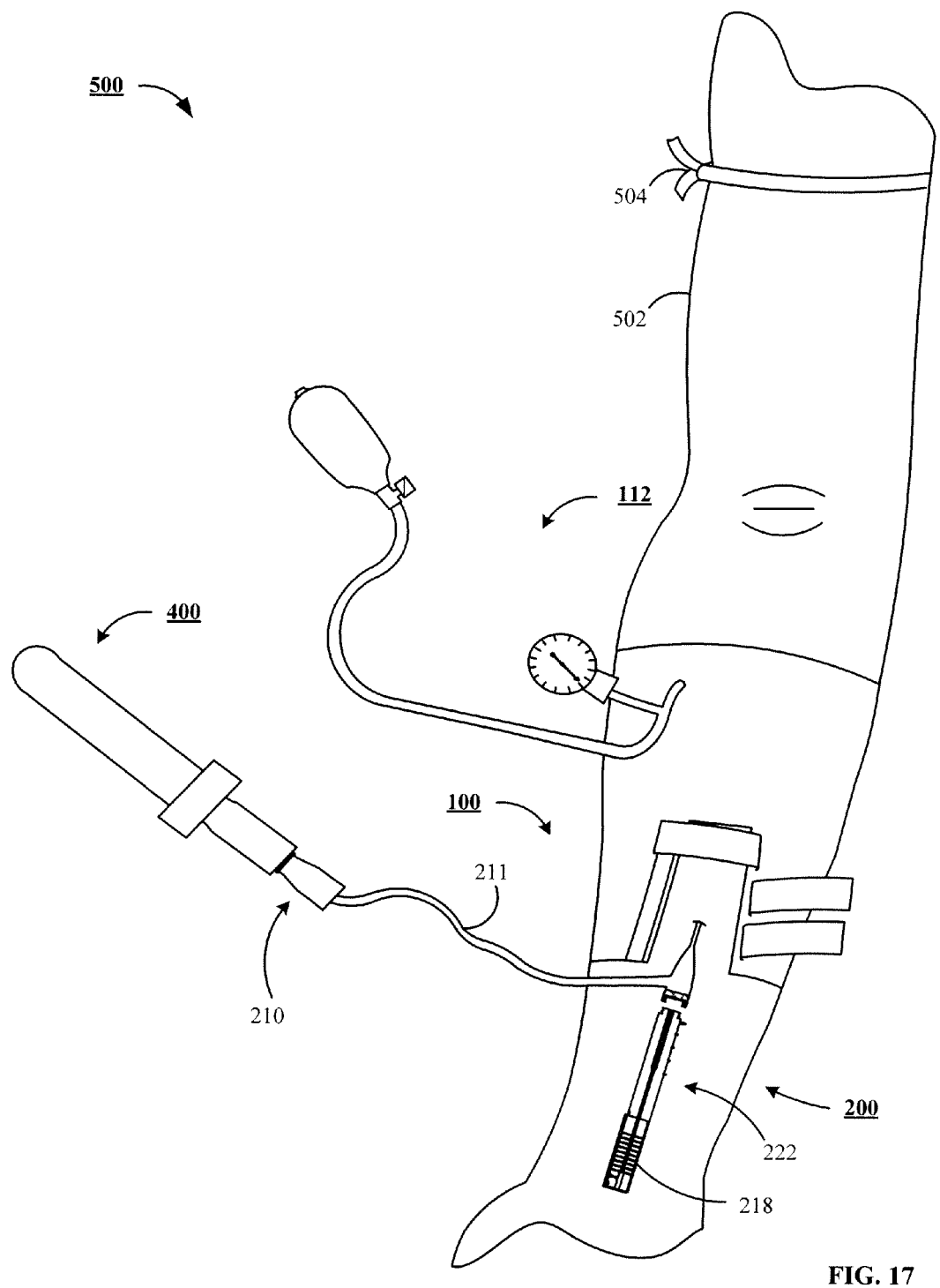
FIG. 17 is a perspective view of a blood vessel access kit in an exemplary embodiment.
Figure 18:
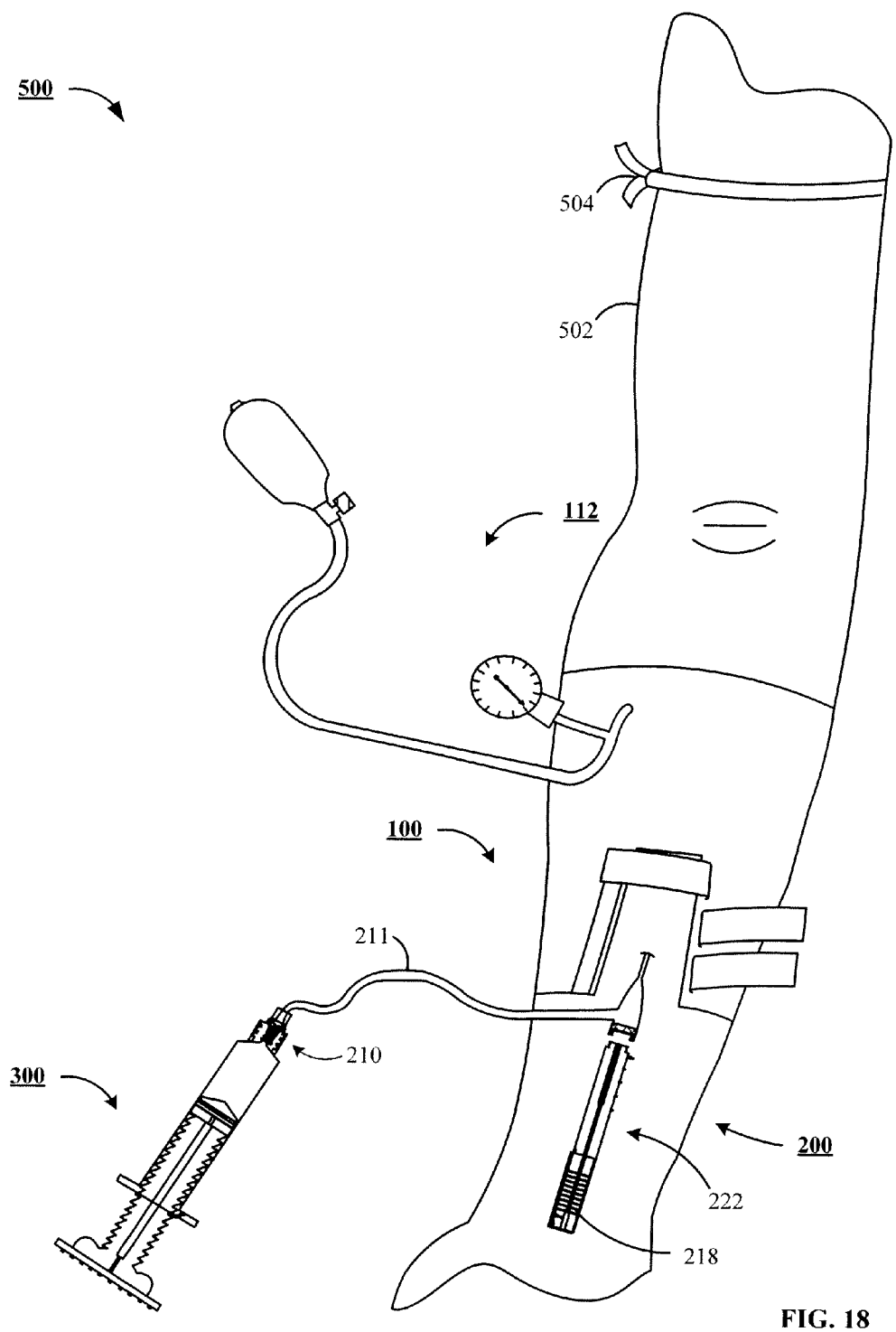
FIG. 18 is a perspective view of a blood vessel access kit in an alternate exemplary embodiment.

FIGS. 17 and 18 show a perspective view of an exemplary blood vessel access kit 500. The exemplary blood vessel access kit 500 preferably includes the exemplary blood channeling apparatus 100 engaging the appendage 502 of a patient. The air transfer assembly 112 is preferably displayed configured to supply air to the exemplary blood channeling apparatus 100. Further in an exemplary embodiment, a tourniquet 504 restricts venous blood flow of the patient. The exemplary intravenous catheter 200 is illustrated communicating with a blood vessel of the patient. The needle confinement housing 222 is preferably shown restricting the needle transport 218. Preferably, the exemplary syringe 300 or the exemplary container 400 is mutually distinct in the ability to transfer fluids from a blood vessel of the patient.

FIG. 19 shows an alternate exemplary intravenous catheter 600, which preferably includes at least a fluid chamber 202 that provides at least one conduit 204 and diaphragm housing 206. In an exemplary embodiment, the diaphragm housing 206 is located on the proximal end of the fluid chamber 202, and the catheter 208 is secured to the distal end of the fluid chamber 202. In a further exemplary embodiment, a needleless valve 210 communicates with the fluid chamber 202 via a fluid transfer tube 211 secured to and disposed between the conduit 204 and the needleless valve 210. The CLAVE® Connector with luer lock, such as those manufactured by ICU Medical Inc. of San Clemente Calif., has been found to be suitable as the needleless valve 210.

FIG. 19 further shows the fluid chamber 202 of the alternate exemplary intravenous catheter 600 preferably has a securement member 212 adjacent the diaphragm housing 206. The alternate exemplary intravenous catheter 600, includes a diaphragm 214 confined in the diaphragm housing 206, and configured to allow passage of a hypodermic needle 216, which extends from a needle transport 218 through the diaphragm 214, the fluid chamber 202, and the catheter 208 when the alternate exemplary intravenous catheter 600 is configured for insertion into a predetermined blood vessel of a patient. The needle transport 218 includes a needle confinement feature 220, which interacts with a needle safety catch feature 224 to secure the hypodermic needle 216 within a needle confinement housing 602, once the hypodermic needle 216 has been extracted from the diaphragm 214.

The alternate exemplary intravenous catheter 600 further includes an exemplary vacuum vessel assembly 604 fitted within and constrained by the needle confinement housing 602 through the use of a securement key 606. Upon removal of the securement key 606, the exemplary vacuum vessel assembly 604 may be advanced relative to the hypodermic needle 216 until the hypodermic needle 216 penetrates through a self-sealing diaphragm 608 fitted within a rigid test tube shaped vessel 610.

The rigid test tube shaped vessel 610 provides access to a vacuum environment provided by the exemplary vacuum vessel assembly 604 of the alternate exemplary intravenous catheter 600. To advance the rigid test tube shaped vessel 610, the exemplary vacuum vessel assembly 604 further provides an advancement tab assembly 612, which interacts with a slide channel 614 provided by the needle confinement housing 602 of the alternate exemplary intravenous catheter 600.

FIG. 20 shows that as an advancement force is applied to the advancement tab assembly 612 of the exemplary vacuum vessel assembly 604, the advancement tab assembly 612 progresses along the slide channel 614. The progression of the advancement tab assembly 612 along the slide channel 614 imparts both a rotational motion and a lateral motion on the rigid test tube shaped vessel 610 relative to the hypodermic needle 216. The collective motions of the rigid test tube shaped vessel 610 promote penetration of the self-sealing diaphragm 608 by the hypodermic needle 216.

FIG. 21 shows the advancement tab assembly 612 of the exemplary vacuum vessel assembly 604 in its maximum advancement position. The advancement tab assembly 612 is shown to include at least a slide shaft 616, that interacts directly with the slide channel 614, and an appendage platform 618 secured to the slide shaft 616. When the advancement tab assembly 612 has attained its maximum extent, the slide shaft 616 is positioned in a second slide channel, which accommodates the exodus of the exemplary vacuum vessel assembly 604 from the needle confinement housing 602 at the conclusion of the medical procedure.

FIG. 22 shows the needle transport 218 of the alternate exemplary intravenous catheter 600 preferably includes a plurality of isolation diaphragms 226 configured to enclose first and second fluid ports 228 and 230 of the hypodermic needle 216, when the needle confinement feature 220 is secured by the needle safety catch feature 224. Further in an exemplary embodiment, a grip portion 232 is provided by the needle transport 218 to facilitate sliding communication of the needle transport 218 with the needle confinement housing 602.

Figure 23:
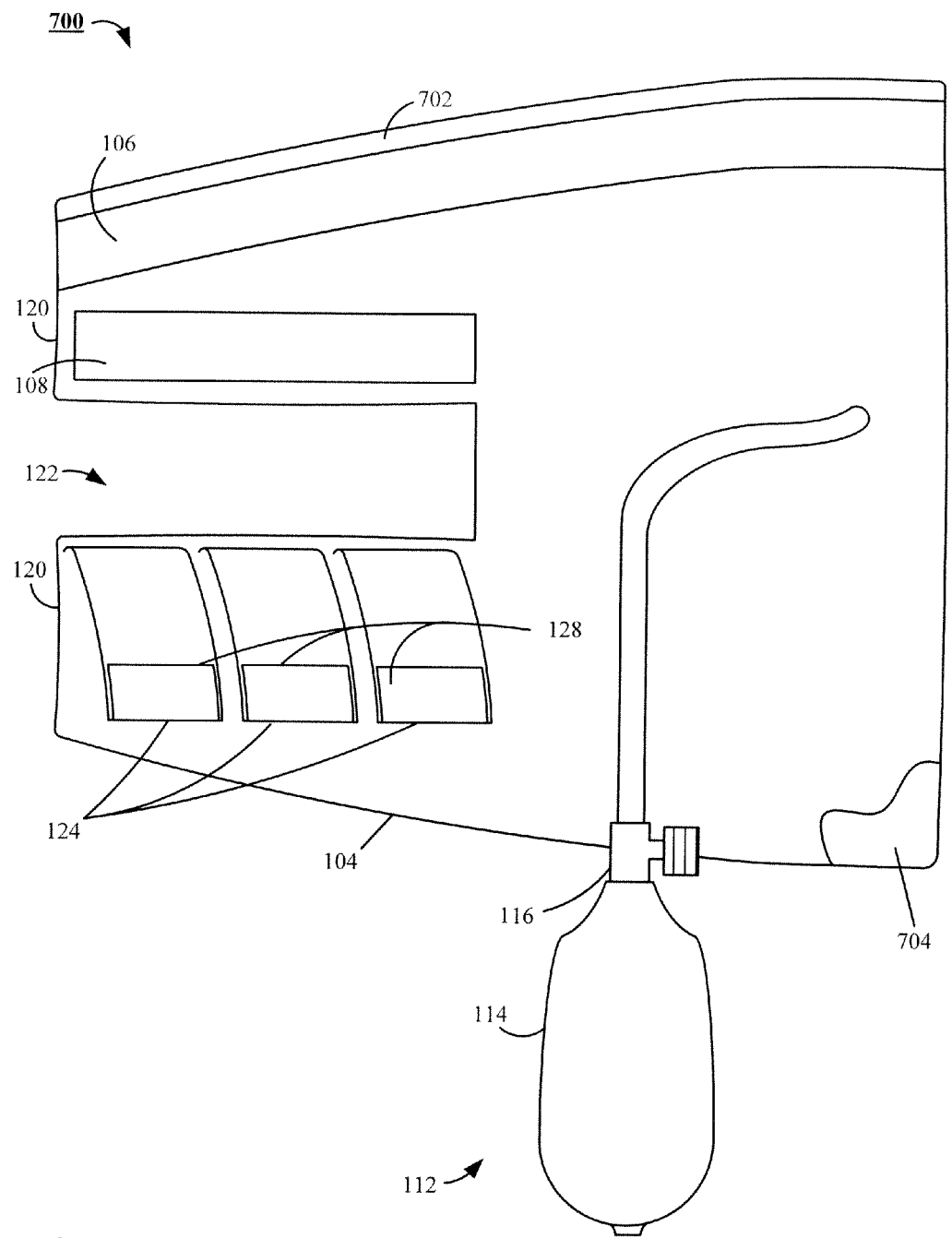
FIG. 23 is a partial cutaway top plan view of the blood channeling apparatus in an alternate exemplary embodiment.

FIG. 23 shows an alternative exemplary blood channeling apparatus 700 of an exemplary embodiment. The alternative exemplary blood channeling apparatus 700 includes an interior cover 702 secured to an exterior cover 704. The exterior cover 704 supports a first securement member 106 and a first fastening member 108. Upon sealing the interior cover 702 secured to the exterior cover 704, an air bladder is formed therebetween. The bladder serves to apply pressure to the extremity of a patient to encourage additional blood into a blood vessel of interest to accommodate the insertion of an intravenous ("IV") catheter into the blood vessel of interest.

To facilitate pressure build up and withdrawal, an air transfer assembly 112 communicates with the formed bladder. The air transfer assembly 112 includes at least an inflation mechanism 114, which may be of a manual or mechanical type; and a valve 116, which selectively controls air flow into and out of the formed bladder.

In an exemplary embodiment, the interior cover 702 and exterior cover 704 join to form a plurality of projections 120 that define a window 122. In an exemplary embodiment, at least one attachment tab 124 is secured to one of the plurality of projections 120 and is configured for engagement with the first fastening member 108 secured to a corresponding projection 120, of the plurality of projections 120.

Figure 24:
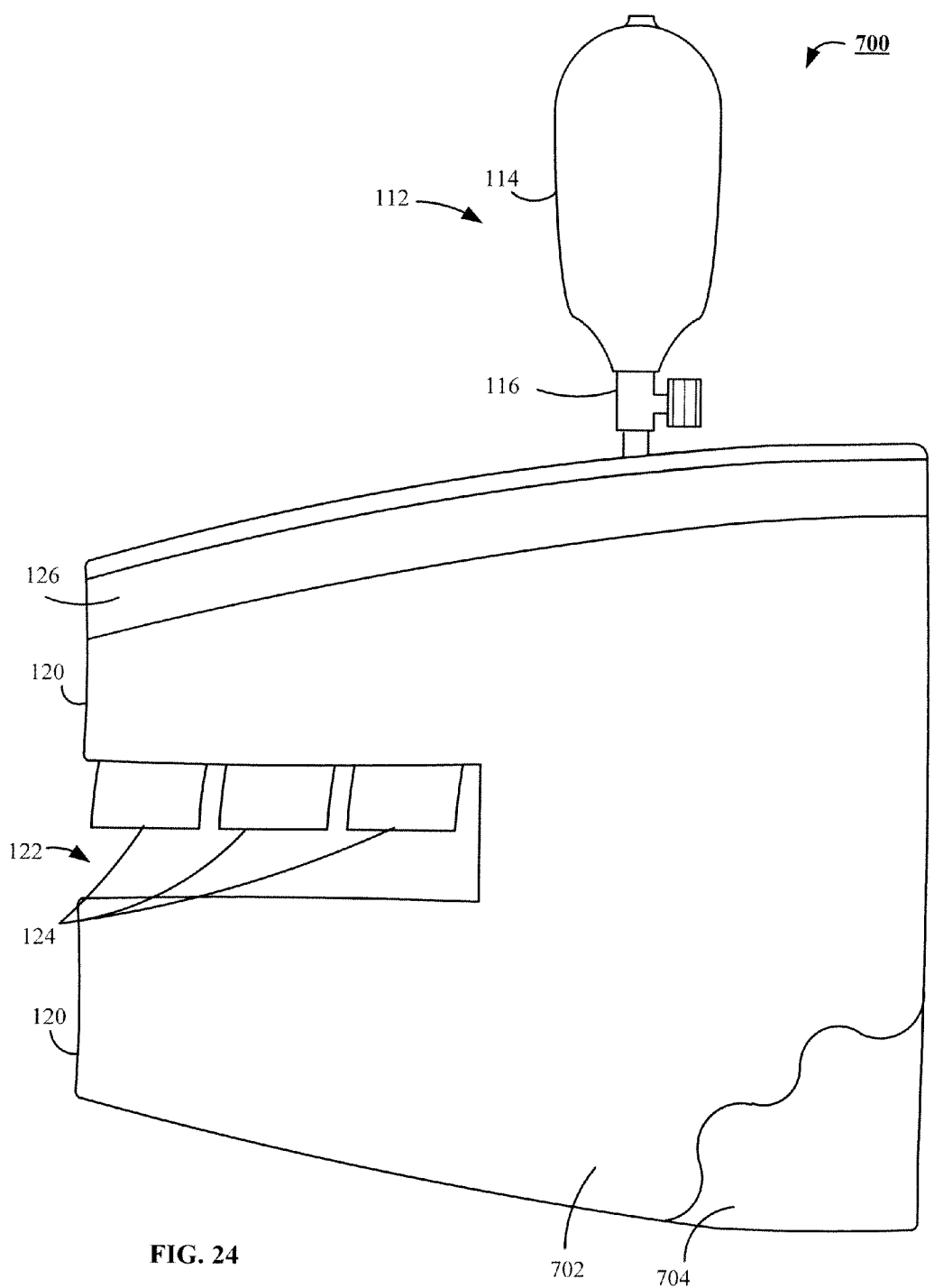
FIG. 24 is a partial cutaway bottom plan view of the alternate exemplary embodiment of the novel blood channeling apparatus of FIG. 23.

FIG. 24 displays a bottom plan view of the alternative exemplary blood channeling apparatus 700 of the exemplary embodiment. A second fastening member 126 is shown secured to the interior cover 702 of the alternative exemplary blood channeling apparatus 700. The second fastening member 126 of the interior cover 702 is preferably configured to connect to the first securement member 106 of the exterior cover 704 to allow the alternative exemplary blood channeling apparatus 700 to surround an extremity of a patient.

Figure 25:
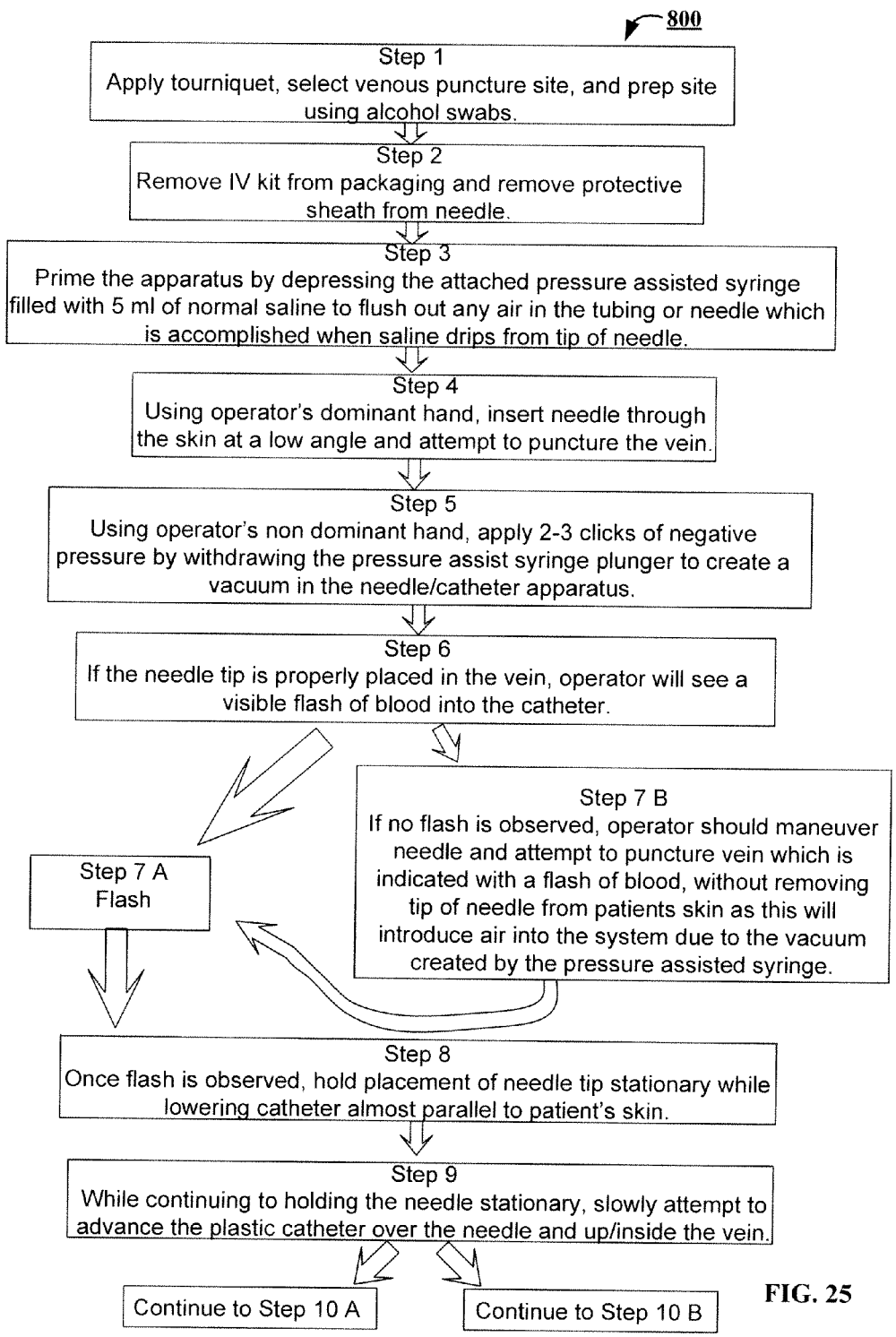
FIG. 25 is a flow diagram disclosing an exemplary method of using the inventive blood vessel access kit Step 1 through Step 9 and continuing to Step 10.

The flow charts, FIGS. 25 through 28, disclose an exemplary method of using the inventive blood vessel access kit. FIG. 25 shows the exemplary process 800 to commence at process Step 1, with the application of a tourniquet to a patient. At process Step 2, prepare a needle for use. At process Step 3, saline is advanced into the needle. Venipuncture is attempted at process Step 4. In process Step 5, create a vacuum in the needle and catheter apparatus. At process Step 6, operator looks for a flash of blood into the catheter. In process Step 7 A, a flash of blood is observed. In the alternative, in process Step 7 B, the needle is maneuvered until a flash of blood is observed (of process Step 7 A). After the flash of blood is observed (of process Step 7 A), the needle tip is held stationary while positioning the catheter in process Step 8. In process step 9, the catheter is advanced over the needle and into the punctured vein. Process Step 10 continues in FIG. 26.

Figure 26:
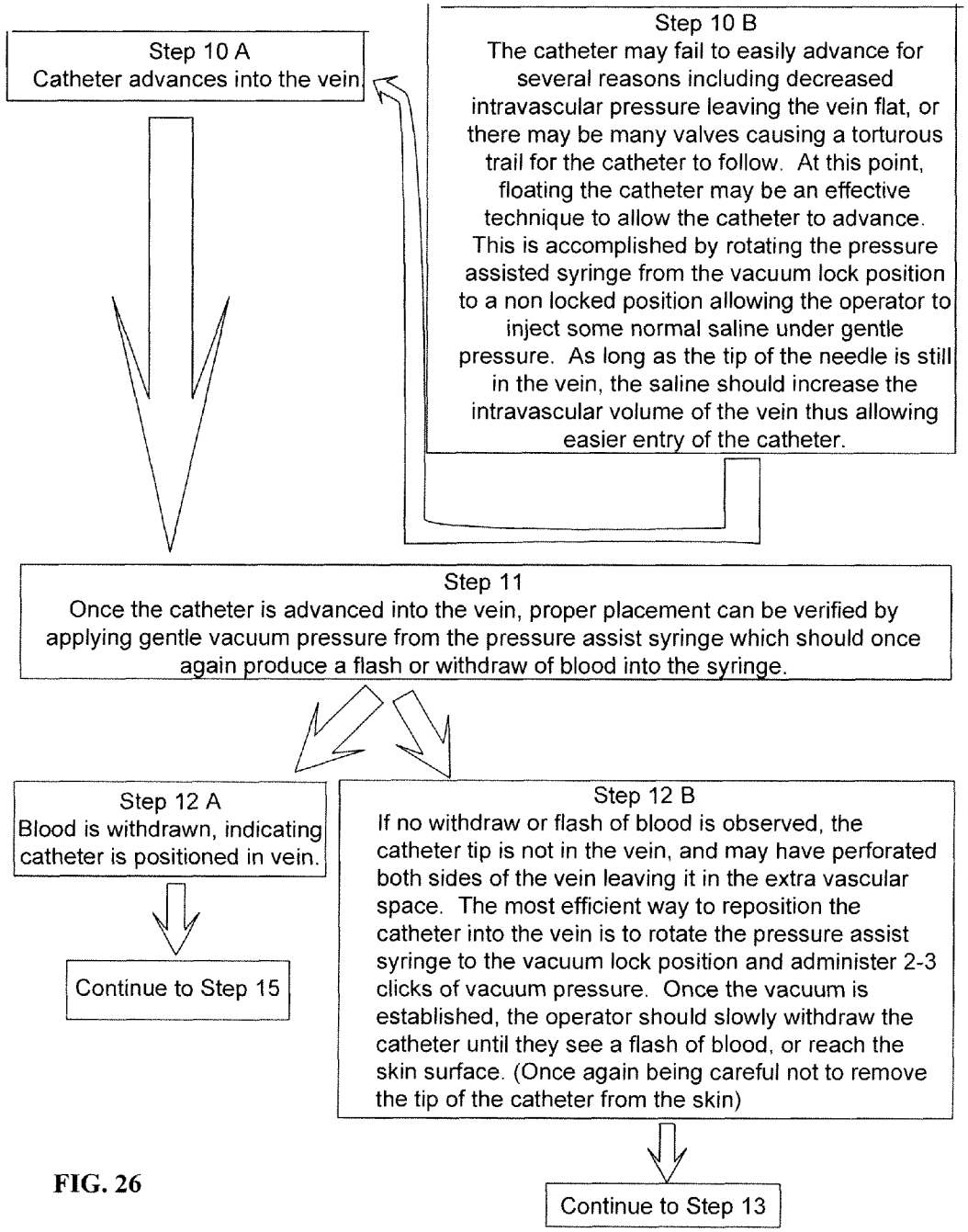
FIG. 26 is a flow diagram disclosing an exemplary method of using the inventive blood vessel access kit Step 10 through Step 12, and continuing to step 13 or in the alternative Step 15.

In FIG. 26, process Step 10 A shows the catheter advances into the vein. In the alternative, in process Step 10 B, the catheter fails to advance easily and the operator maneuvers the catheter so that it will advance. Process Step 11 shows that proper placement of the advanced catheter (of process Step 10 A) can be verified once the catheter is advanced into the vein. In process Step 12 A, blood is withdrawn, and the exemplary process 800 continues at process Step 15. In the alternative, in process Step 12 B, no withdraw or flash of blood is observed, so the catheter is repositioned, and the exemplary process 800 continues at process Step 13 in FIG. 27.

Figure 27:
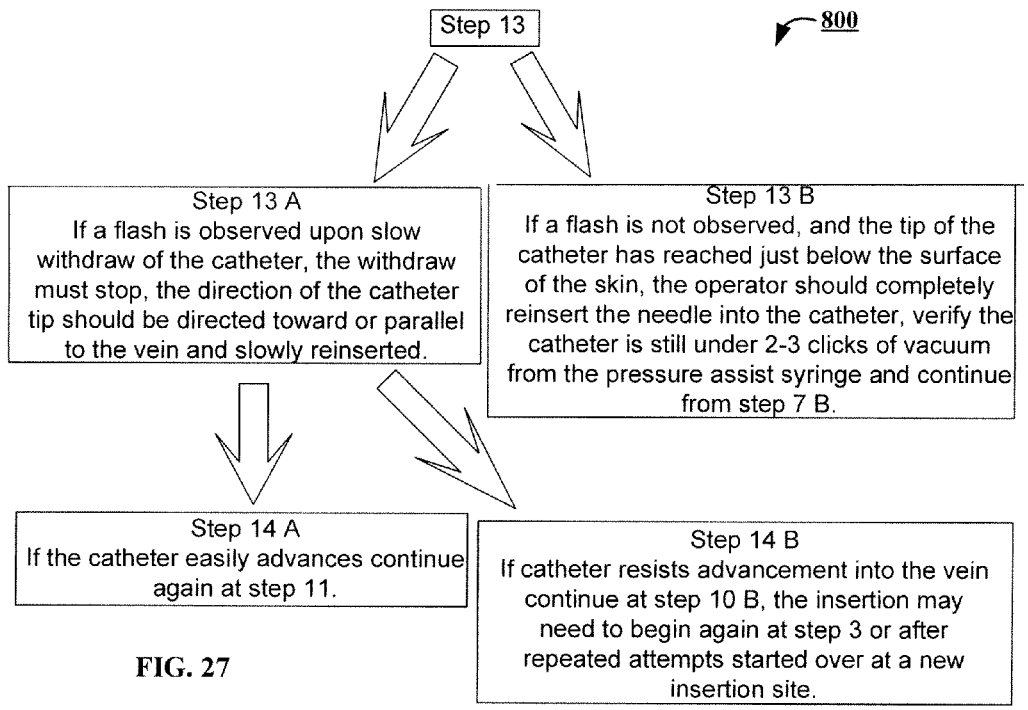
FIG. 27 is a flow diagram disclosing an exemplary method of using the inventive blood vessel access kit Step 13 through Step 14.

In FIG. 27, process Step 13 A shows catheter is repositioned after seeing a flash of blood and in process Step 14 A the catheter easily advances so the operator continues from process Step 11 (of FIG. 26), or in the alternative if the catheter resists advancement the operator may need to continue with process Step 10 B (of FIG. 26), process Step 3 (of FIG. 25), or process Step 1 (of FIG. 25). In the alternative, in process Step 13 B, no flash of blood is observed so the operator returns to process Step 7 B (of FIG. 25).

Figure 28:
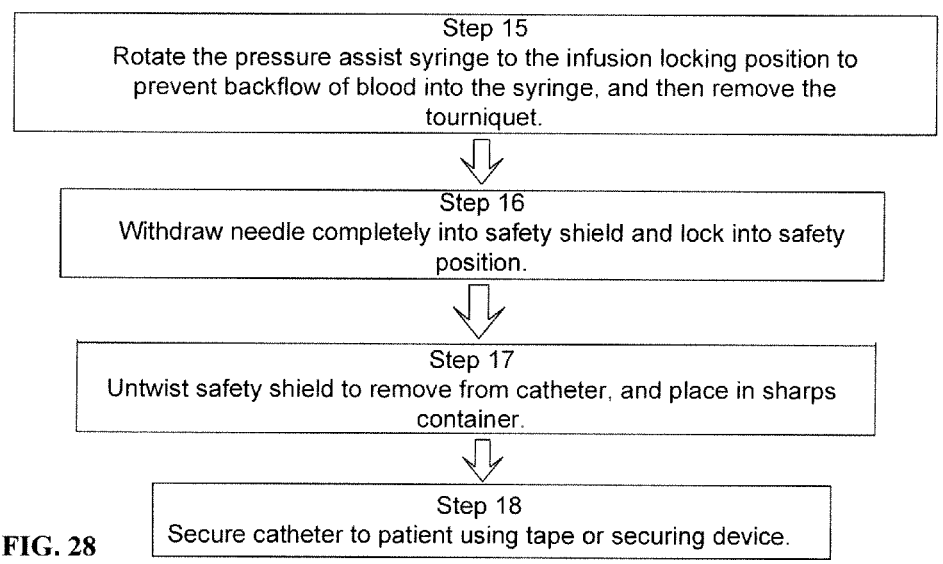
FIG. 28 is a flow diagram disclosing an exemplary method of using the inventive blood vessel access kit Step 15 through Step 18.

In FIG. 28, process Step 15 shows infusion locking position is achieved and the tourniquet is removed. At process Step 16, the needle is withdrawn into a safety shield. In process Step 17, the safety shield is disposed of in a sharps container. At process Step 18, the catheter is secured to the patient.

While the process Steps of exemplary process 800 are meant to be exemplary, numerous changes to the Steps, and also the sequencing of the Steps, may be made which will readily suggest themselves to those skilled in the art and which are encompassed by the appended claims.

FIG. 29 shows a top plan view of a preferred vein presentation enhancement device 820, which includes at least an exterior cover 822 that provides a first securement member 824 supported by a web 826. In a preferred embodiment, the web 826 is formed from a polyvinylchloride ("PVC") material, and the first securement member 824 is the loop portion of a hook and loop fastening system formed from a polymer and adhered to the web 826. FIG. 29 further shows that the exterior cover 822 preferably provides an access aperture 828 through which a conduit interface member 830 is feed-through from the back side and secured to the web 826 by a heat seal 832. FIGS. 30, 31, and 32 respectively show the preferred conduit interface member 830 in a top plan view, bottom plan view, and view in elevation, which is preferably formed from PVC. The stitching 834, shown in FIG. 29 is a preferred means of securing a preferred first fastening member 836 (shown by FIG. 33) to each an interior cover 838 (of FIG. 33), and the exterior cover 822.

Figure 33:
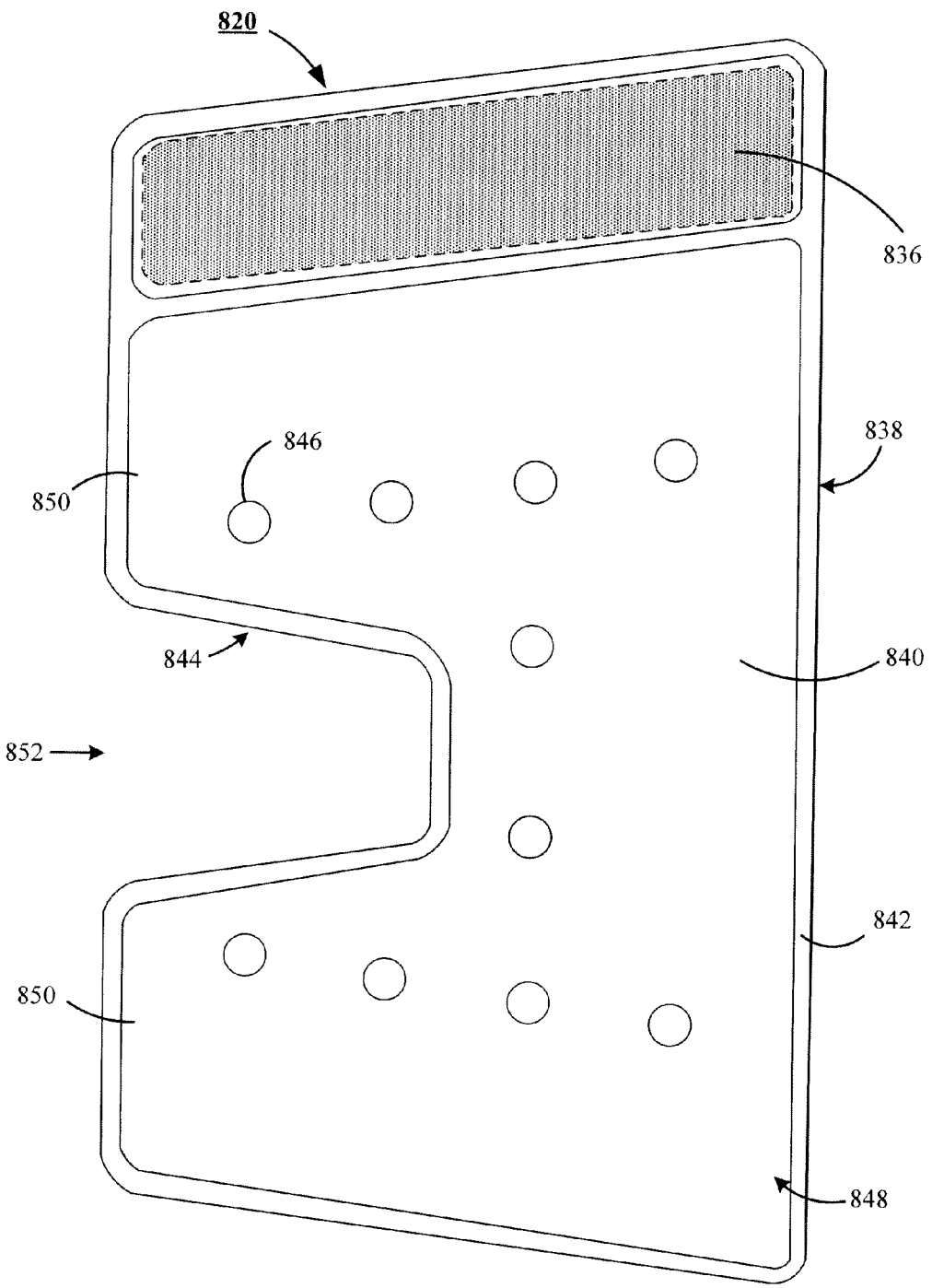
FIG. 33 is a bottom plan view of the alternative alternate exemplary embodiment of the inventive vein presentation enhancement device of FIG. 29.

As further shown by FIG. 33, the interior cover 838 provides a patient contact material 840 supported by a web 842. In a preferred embodiment, the web 842 is formed from a PVC material; the patient contact material 840 is formed from cotton and adhered to the web 842. Preferably, the first fastening member 836 provided the hook portion of a hook and loop fastening system, and is formed from a polymer. In a preferred embodiment, the interior cover 838 is secured to the exterior cover 822 by a heat seal 844 and a plurality of strain relief features 846. A preferred result of completion of the heat seal process is the formation of an air tight bladder 848, and at least two projections 850, which collectively define a blood access window 852.

The vein presentation enhancement device 820, is preferably configured such that when wrapped in secure contact around a limb of a patient with the first fastening member 836 secured to the first securement member 824, upon inflating the bladder the first fastening member 836 will self release from the first securement member 824 at a pressure of about 195 to 220 mmHg, thereby mitigating an ill effect of overinflating the vein presentation enhancement device 820.

Figure 34:
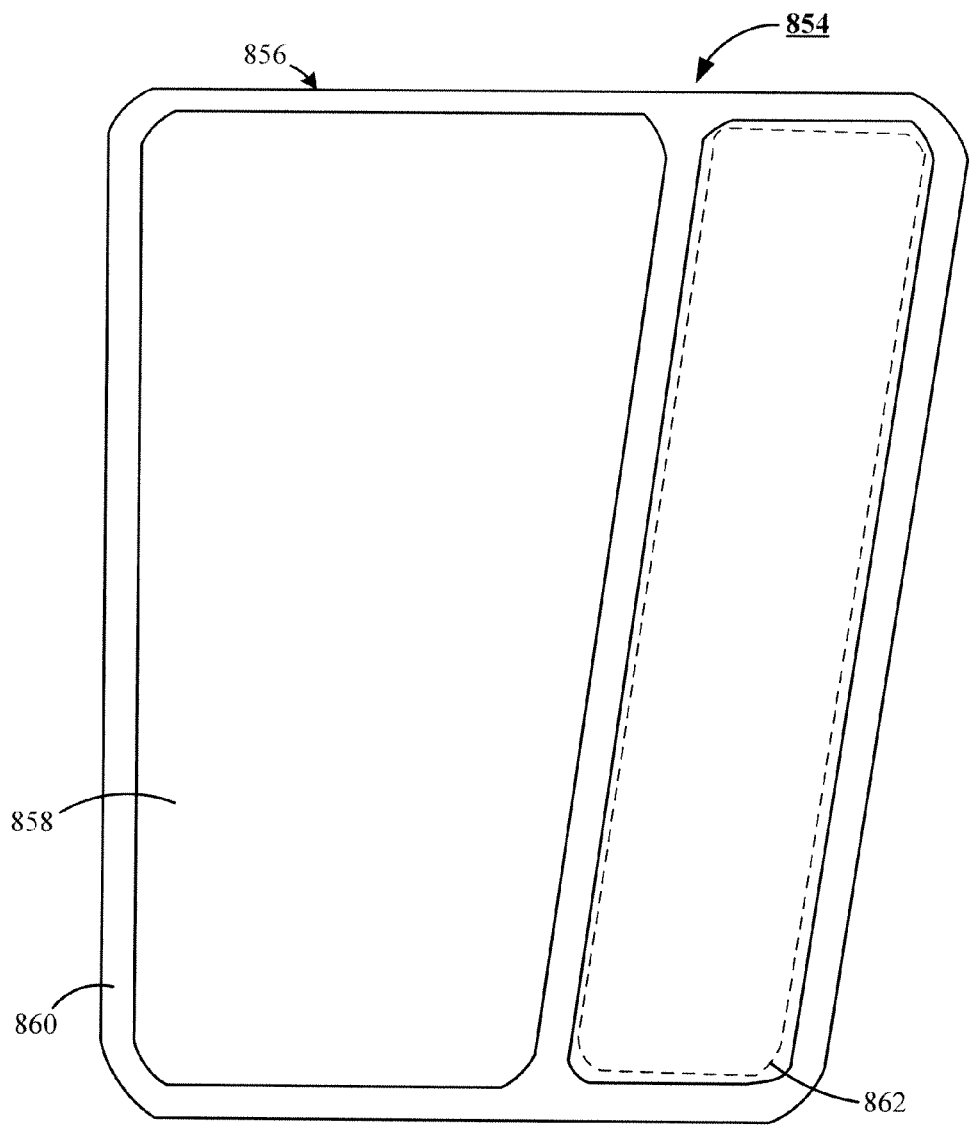
FIG. 34 is a top plan view of an extension member configured for use with the alternative alternate exemplary embodiment of the inventive vein presentation enhancement device of FIG. 29.

FIG. 34 shows a top plan view of a preferred extension member 854 for the vein presentation enhancement device 820, which includes at least an exterior extension cover 856 that provides a second securement member 858 supported by an exterior extension web 860. In a preferred embodiment, the exterior extension web 860 is formed from a PVC material, and the second securement member 858 is the loop portion of a hook and loop fastening system formed from a polymer and adhered to the exterior extension web 860. The stitching 862, shown in FIG. 34 is a preferred means of securing a preferred second fastening member 866 (shown by FIG. 35) to each an interior extension cover 868 (of FIG. 35), and the exterior extension cover 856.

Figure 35:
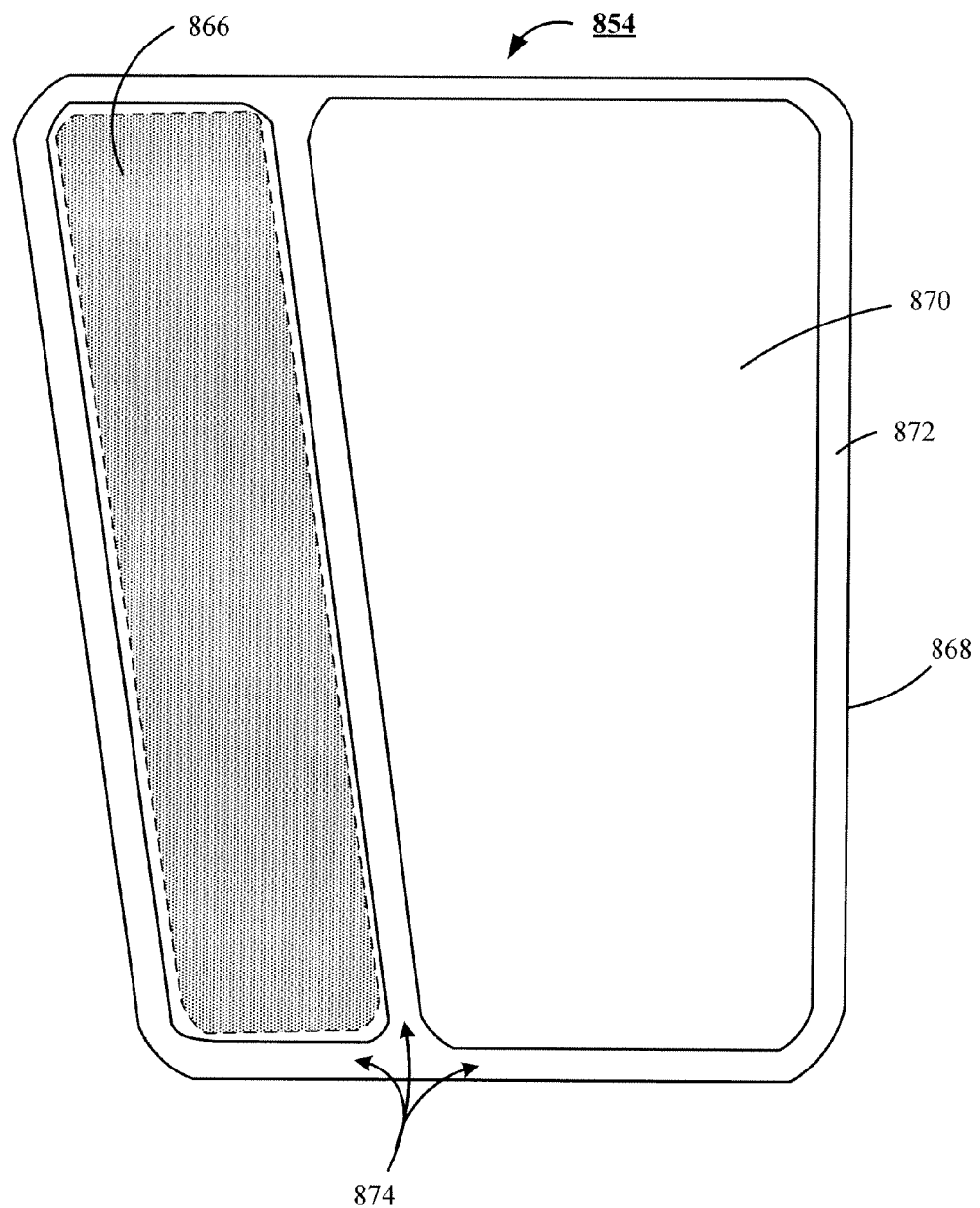
FIG. 35 is a bottom plan view of the extension member of FIG. 34.

As further shown by FIG. 35, the interior extension cover 868 provides a patient contact extension material 870 supported by an interior extension web 872. In a preferred embodiment, the interior extension web 872 is formed from a PVC material; the patient contact extension material 870 is formed from cotton and adhered to the interior extension web 872. Preferably, the second fastening member 866 provided the hook portion of a hook and loop fastening system, and is formed from a polymer. In a preferred embodiment, the interior extension cover 868 is secured to the exterior extension cover 856 by a heat seal 874.

Figure 36:
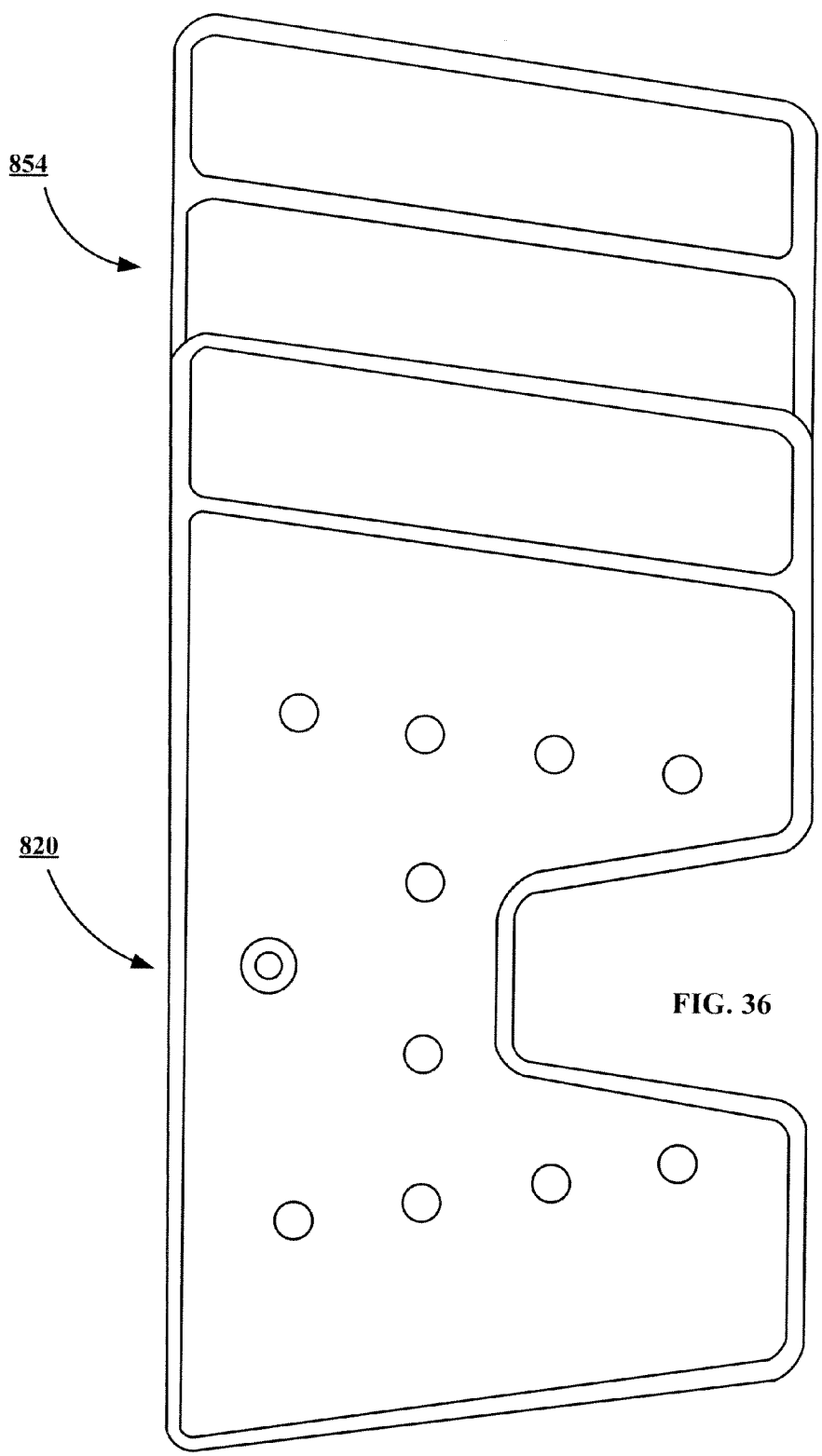
FIG. 36 is a bottom plan view of the alternative alternate exemplary embodiment of the inventive vein presentation enhancement device of FIG. 29.

FIG. 36 shows the preferred vein presentation enhancement device 820 secured to the preferred extension member 854. To facilitate this securement, the first fastening member 836 of the vein presentation enhancement device 820 provides the hook portion of a hook and loop fastening system, and the second securement member 858 of the extension member 854 provides the loop portion of the hook and loop fastening system. The result of adding the extension member 854 to the preferred vein presentation enhancement device 820 is an accommodation of various limbs, or portion of limbs, of patients. With the extension member 854 attached, the inflatable tourniquet (vein presentation enhancement device 820) becomes functional by securing the second fastening member 866 (of FIG. 35) to the first securement member 836 (of FIG. 33)

Figure 37:
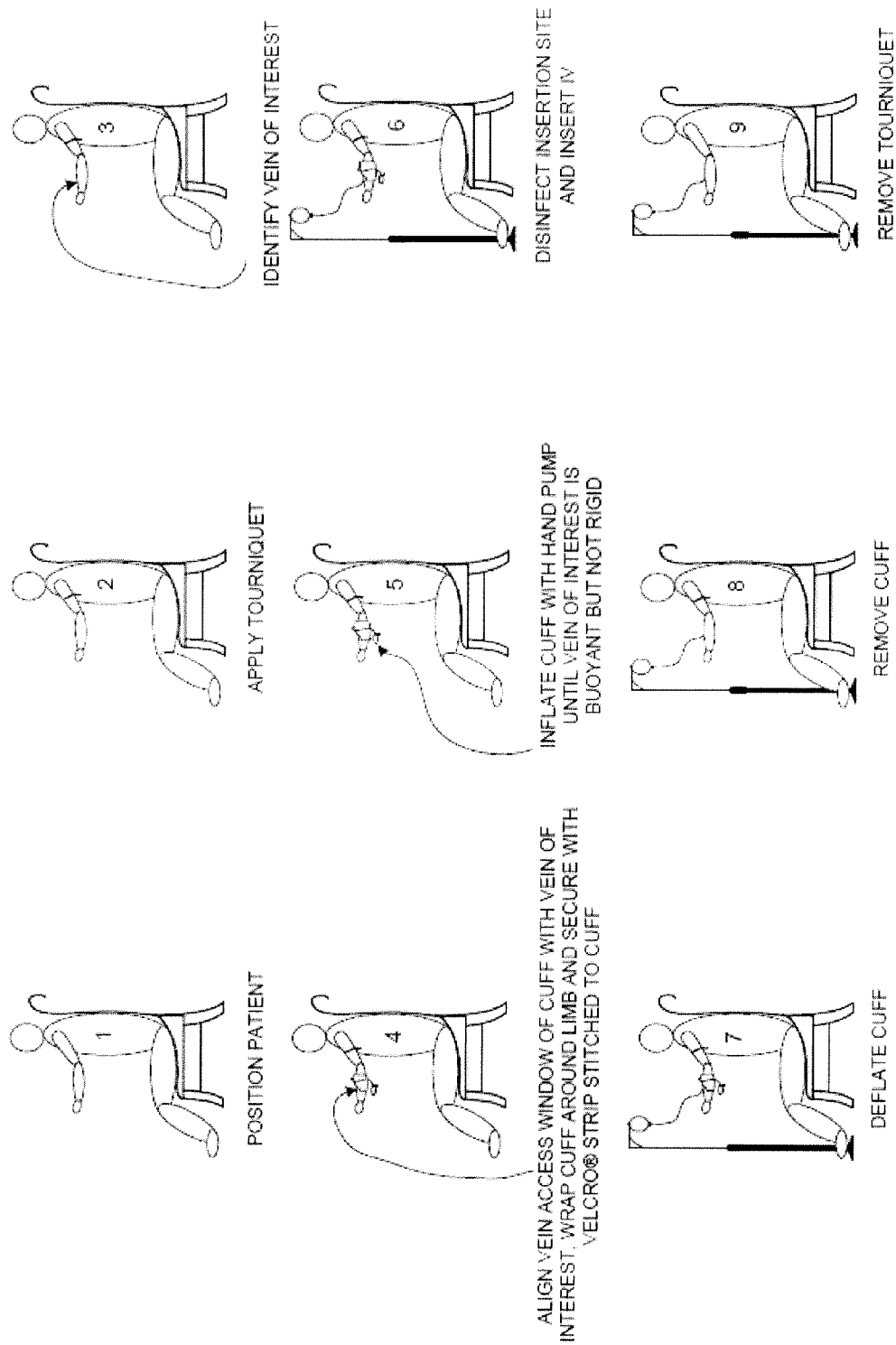
FIG. 37 is a flow diagram of a method of using the inventive vein presentation enhancement device of FIG. 29 for starting an IV.
Figure 38:
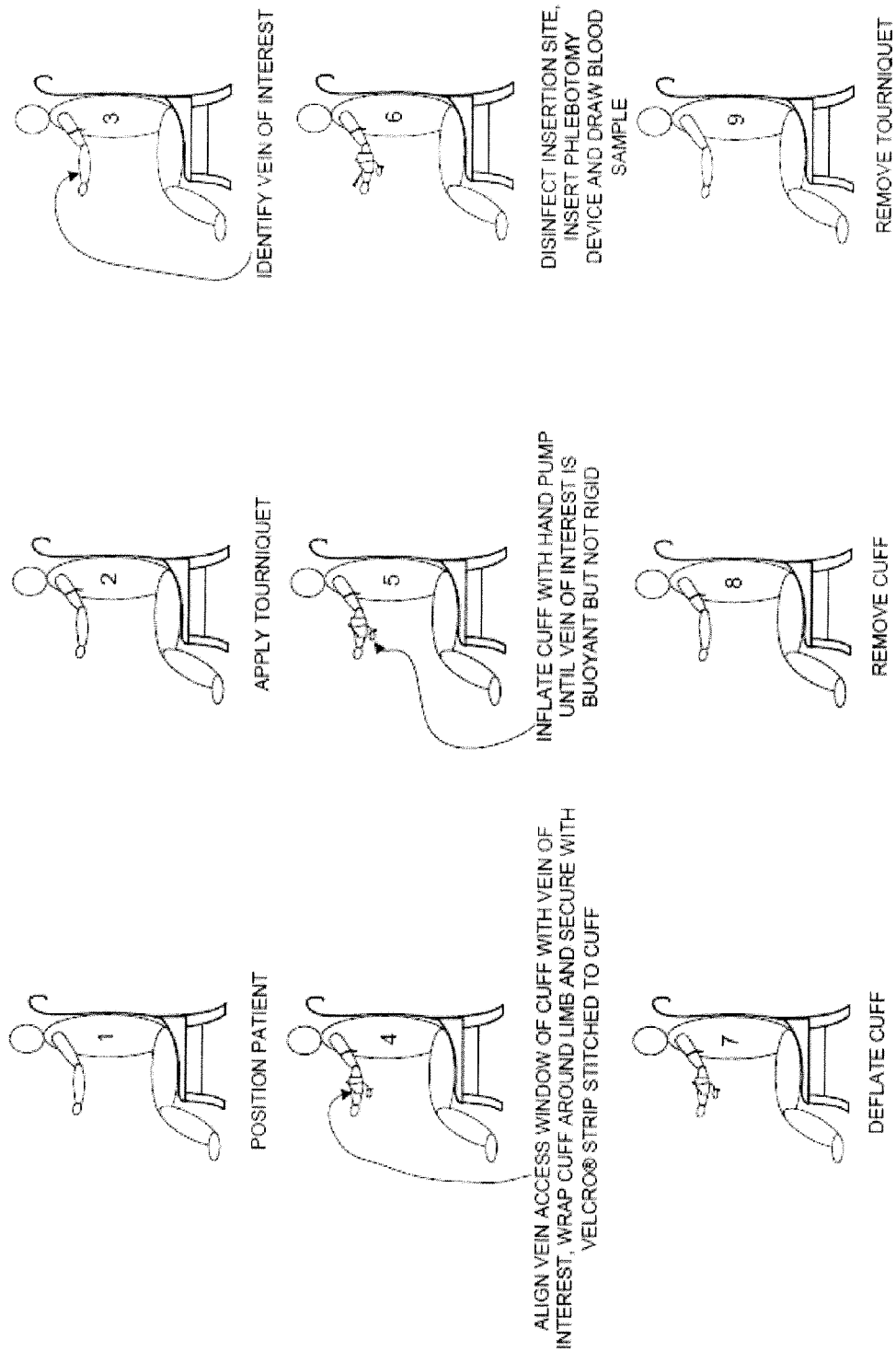
FIG. 38 is a flow diagram of an alternate method of using the inventive vein presentation enhancement device of FIG. 29 for drawing blood.

FIG. 37 illustrates a flow diagram of a method of using the inventive vein presentation enhancement device 820 (of FIG. 29), in starting an IV in a patient, while FIG. 38 shows a flow diagram of an alternate method of using the inventive vein presentation enhancement device 820 of FIG. 29 in drawing blood from a patient.

Figure 39:
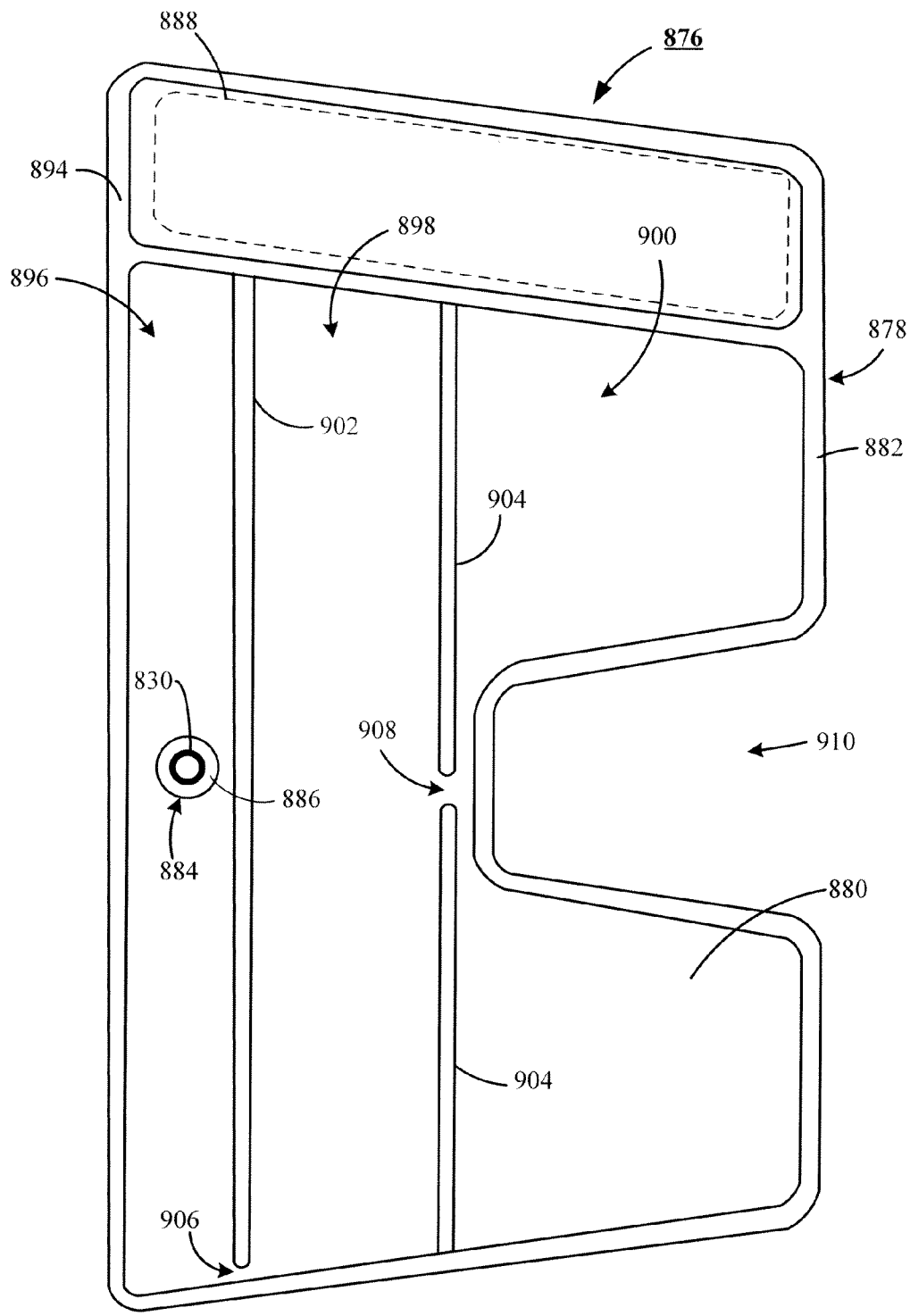
FIG. 39 is a top plan view of another alternate exemplary embodiment of a novel blood channeling apparatus, also referred to as a vein presentation enhancement device.

FIG. 39 shows a top plan view of a preferred vein presentation enhancement device 876, which includes at least an exterior cover 878 that provides a first securement member 880 supported by a web 882. In a preferred embodiment, the web 882 is formed from a polyvinylchloride ("PVC") material, and the first securement member 880 is the loop portion of a hook and loop fastening system formed from a polymer and adhered to the web 882. FIG. 39 further shows that the exterior cover 878 preferably provides an access aperture 884 through which a conduit interface member 830 (of FIGS. 30, 31, and 32) is feed-through from the back side of the exterior cover 878 and secured to the web 882 by a heat seal 886. FIGS. 30, 31, and 32 respectively show the preferred conduit interface member 830 in a top plan view, bottom plan view, and view in elevation, which is preferably formed from PVC. The stitching 888, shown in FIG. 39 is a preferred means of securing a preferred fastening member 890 (shown by FIG. 40) to each an interior cover 892 (of FIG. 40), and the exterior cover 878.

FIG. 39 further shows that heat seal 894 provides the external boundaries for each of the plurality of bladders, which in the present embodiment include, stage I bladder 896, stage II bladder 898, and stage III bladder 900. Heat seal portion 902 forms the boundary and substantial fluidic seal between stage I bladder 896 and stage II bladder 898, while heat seal portion 904 forms the boundary and substantial fluidic seal between stage II bladder 898 and stage III bladder 900. To facilitate a substantially sequential filling of stage I, II, and III bladders of the present exemplary embodiment, a first fluidic conduit 906 is provided to promote passage of fluid from stage I bladder 896 to stage II bladder 898, once the volume and pressure of fluid in stage I bladder 896 reaches a predetermined level. Likewise, a second fluidic conduit 908 is provided to promote passage of fluid from stage II bladder 898 to stage III bladder 900, once the volume and pressure of fluid in stage II bladder 898 reaches a predetermined level. This substantial sequential inflation of bladders 896, 898, and 900, serve to encourage blood into veins accessible through the vein access window 910, while mitigating blood flow away from the vein access window 910.

Figure 40:
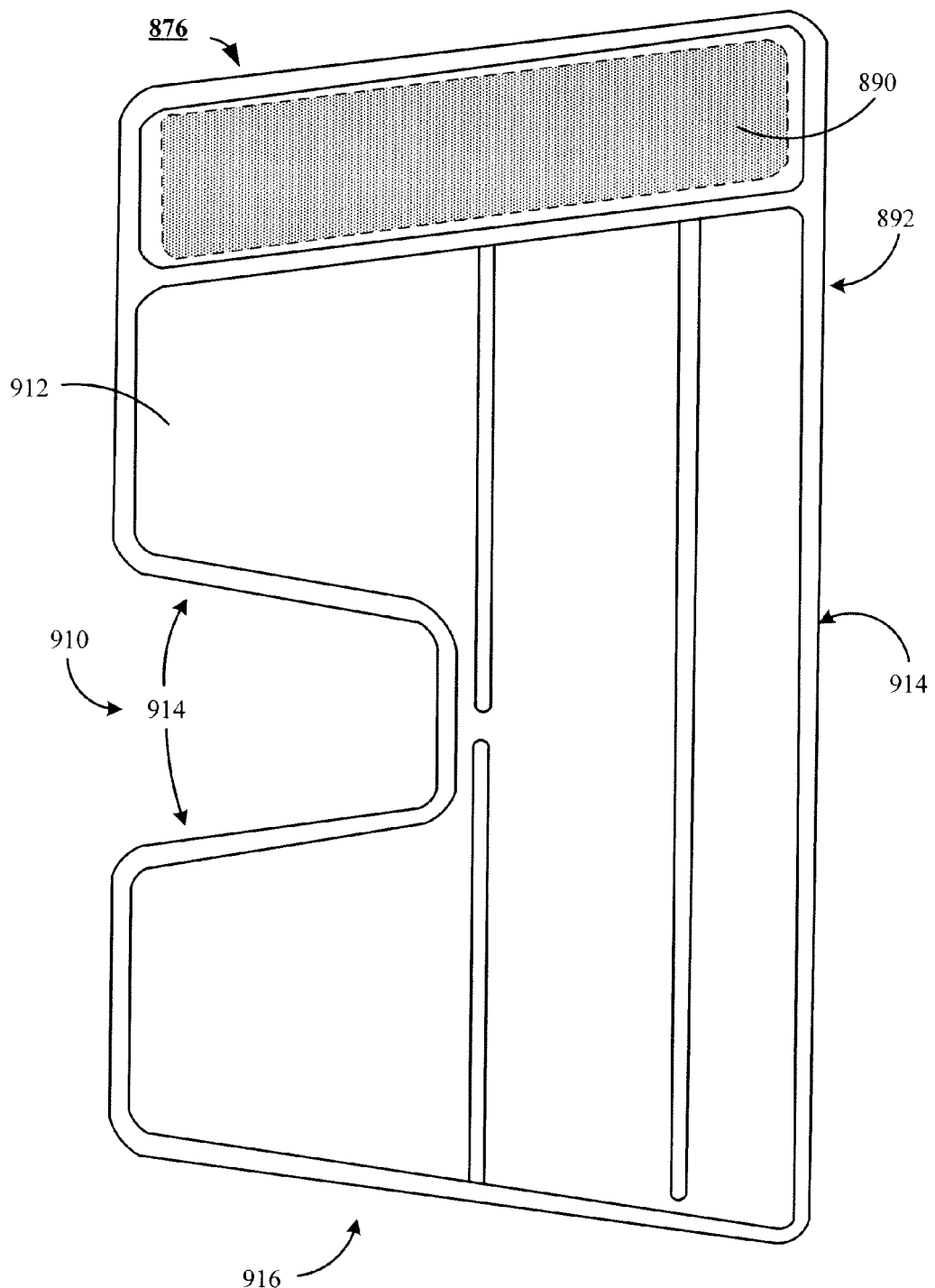
FIG. 40 is a bottom plan view of the novel blood channeling apparatus of FIG. 39, also referred to as a vein presentation enhancement device.

As further shown by FIG. 40, the interior cover 892 provides a patient contact material 912 supported by a web 914. In a preferred embodiment, the web 914 is formed from a PVC material; the patient contact material 912 is formed from cotton and adhered to the web 914. Preferably, the fastening member 890 provided the hook portion of a hook and loop fastening system, and is formed from a polymer. In a preferred embodiment, the interior cover 8892 is secured to the exterior cover 878 by the heat seal 894 and the heat seal portions 902 and 904. A preferred result of completion of the heat seal process is the formation of bladders 896, 898, and 900, which collectively an air tight composite bladder 916 that includes and at least two projections 918, which collectively define the blood access window 910.

Figure 41:
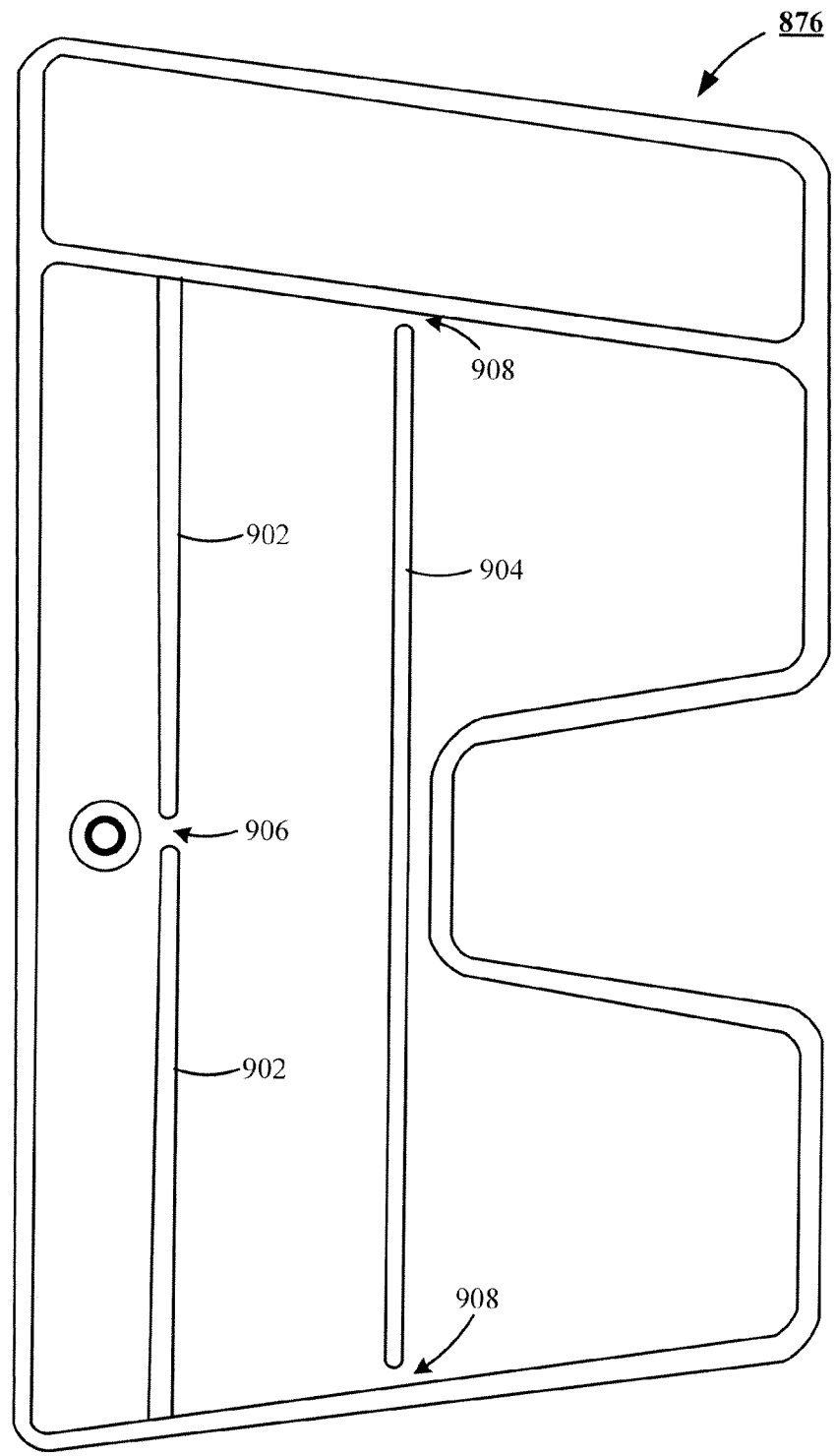
FIG. 41 is a top plan view of another alternative exemplary embodiment of a novel blood channeling apparatus, also referred to as a vein presentation enhancement device.

FIG. 41 shows an exemplary embodiment in which the first fluidic conduit 906 is positioned near the mid portion of heat seal 902, while the second fluidic conduit 908 is disposed adjacent opposite ends of heat seal 904. However, the functionality of fluidic conduits 906 and 908 remain consistent with the explanation provided hereinabove.

It will be clear that the present invention is well adapted to attain the ends and advantages mentioned as well as those inherent therein. While presently exemplary embodiments have been described for purposes of this disclosure, numerous changes may be made which will readily suggest themselves to those skilled in the art and which are encompassed by the appended claims.

What is claimed is:

1. A vein presentation enhancement apparatus comprising:
an interior cover supporting a fastening member;
an exterior cover communicating with said interior cover, said exterior cover providing a securement member;
an air tight composite bladder formed between said interior and exterior covers, wherein the air tight composite bladder comprises a stage I bladder, a stage II bladder, and stage III bladder;
a first fluidic conduit disposed between the stage I bladder and the stage II bladder, wherein the first fluidic conduit promotes passage of fluid from the stage I bladder to the stage II bladder once the volume and pressure of fluid in the stage I bladder reaches a predetermined level;
a second fluidic conduit disposed between the stage II bladder and the stage III bladder, wherein the second fluidic conduit promotes passage of fluid from the stage II bladder to the stage III bladder once the volume and pressure of fluid in the stage II bladder reaches a predetermined level;
a vein access window adjacent to the stage III bladder; and
an air transfer assembly connected to the stage I bladder for transfer of transferring air into and out of the air tight composite bladder, wherein the transfer of air into the air tight composite bladder sequentially inflates the stage I bladder, the stage II bladder, and the stage III bladder.

2. The vein presentation enhancement apparatus of claim 1, wherein the securement member comprises a hook portion of a hook and loop fastening system.

3. The vein presentation enhancement apparatus of claim 1, wherein said fastening member is loop portions of a hook and loop fastening system.

4. The vein presentation enhancement apparatus of claim 1, further comprising a plurality of bladder boundary structures, said boundary structures secure said interior cover to said exterior cover.

5. The vein presentation enhancement apparatus of claim 1, wherein said air transfer assembly comprises:
   an inflation mechanism;
   a valve secured to said inflation mechanism; and
   a conduit disposed between said inflation mechanism and said stage I bladder, said conduit transferring air between said inflation mechanism and said stage I bladder.

6. The vein presentation enhancement apparatus of claim 1, wherein the sequential inflation of the stage I bladder, the stage II bladder, and the stage III bladder encourages a user's blood into veins accessible through the vein access window while mitigating blood flow away from the vein access window.

7. The vein presentation enhancement apparatus of claim 1, wherein upon surrounding a limb of a subject with the air tight composite bladder such that said interior cover is directly adjacent said limb and upon securing said fastening member to said securement member a pneumatic tourniquet is formed.

8. The vein presentation enhancement apparatus of claim 1, further comprising a conduit interface member secure to said exterior cover and communicating with said air transfer assembly to facilitate said transfer of air into and out of the air tight composite bladder.

\* \* \* \* \*